Figure 1:
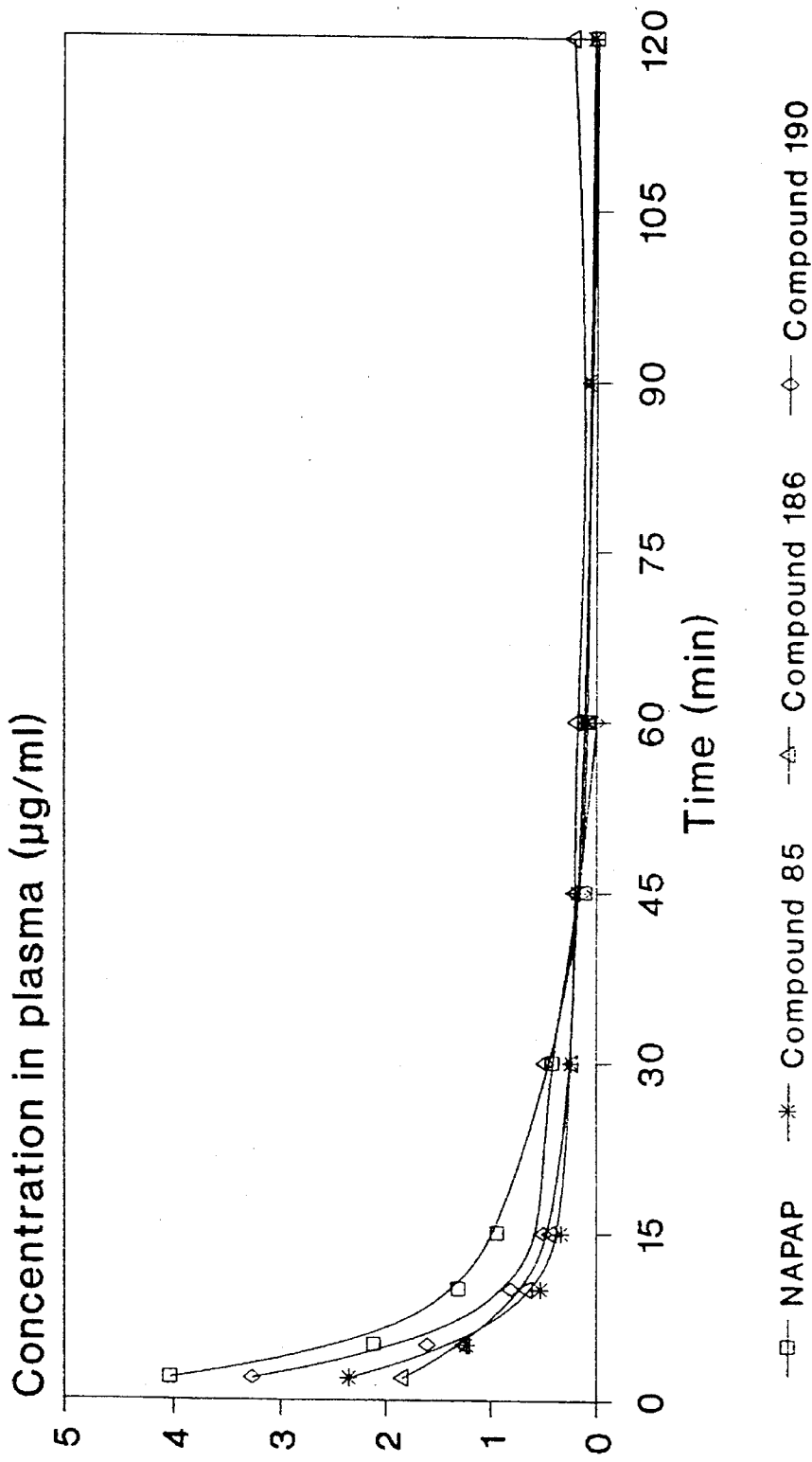

United States Patent [19]

Stürzebecher et al.

[11] Patent Number: 5,518,735
[45] Date of Patent: May 21, 1996

[54] META-SUBSTITUTED PHENYLALANINE DERIVATIVES

[75] Inventors: Jörg Stürzebecher, Erfurt-Rhoda; Helmut Vieweg, Rheinfelden, both of Germany; Peter Wikstroem, Oberwil, Switzerland

[73] Assignee: Pentapharm AG, Basel, Switzerland

[21] Appl. No.: 910,087

[22] PCT Filed: Nov. 15, 1991

[86] PCT No.: PCT/CH91/00235

§ 371 Date: Feb. 10, 1993

§ 102(e) Date: Feb. 10, 1993

[87] PCT Pub. No.: WO92/08709

PCT Pub. Date: Mar. 29, 1992

[30] Foreign Application Priority Data

Nov. 15, 1990 [CH] Switzerland ............................. 3634/90
Jan. 22, 1991 [CH] Switzerland ............................. 0171/91
Mar. 15, 1991 [CH] Switzerland ............................. 0797/91
May 13, 1991 [CH] Switzerland ............................. 1424/91

[51] Int. Cl.$^6$ .................... A61F 13/04; C07C 313/00
[52] U.S. Cl. .................... 424/449; 424/435; 424/436; 424/451; 424/464; 424/489; 514/255; 514/307; 514/316; 514/327; 514/423; 544/386; 544/391; 546/145; 546/189; 546/206; 548/532; 548/533; 548/535; 548/536; 558/61
[58] Field of Search ..................... 546/145, 189, 546/206; 544/386, 391; 548/532, 533; 558/535–536, 61; 514/255, 327, 316, 307, 423; 424/464, 435, 436, 451, 449, 489

[56] References Cited

U.S. PATENT DOCUMENTS 4,125,604 11/1978 Okamoto et al. ..................... 424/177

FOREIGN PATENT DOCUMENTS 2007663 5/1979 United Kingdom.
2153825 8/1985 United Kingdom.

OTHER PUBLICATIONS

G. Wagner et al., Die Pharmazie, 36, No. 9, Sep., 1981, pp. 597–603.
J. Sturzebecker et al., Die Pharmazie, vol. 36, No. 9, Sep. 1981, pp. 639–641.
J. Sturzebecker et al., Thrombosis Research, vol. 54, No. 3, May 15, 1989, pp. 245–252.
H. Vieweg et al., Die Pharmazie, vol. 42, No. 4, Apr. 1987, p. 268.
J. Hauptmann et al., Thrombosis and Haemostasis, vol. 63, No. 2, Apr. 12, 1990, pp. 220–223.
Chemical Abstracts No. 40333V, vol. 107, No. 5, Aug. 3, 1987.
Chemical Abstracts No. 107770B, vol. 98, No. 13, Mar. 28, 1983.

*Primary Examiner*—Jyothsna Venkat
*Attorney, Agent, or Firm*—Pennie & Edmonds

[57] ABSTRACT

D,L-, L- and D-phenyl alanine derivatives of formula (I) defined in claim 1 in which $R_1$ is an amidino-, guanidino-, oxamidino-, aminomethyl- or amino group have been discovered which effectively prevent blood coagulation or thrombosis. The antithrombotically active compounds have low toxicity and may be administered by mouth, subcutaneously or intravenously.

10 Claims, 3 Drawing Sheets

Plasma levels of NAPAP, 85, 186 and 190 after i.v. injection of 1 mg/kg in rats

Plasma levels of NAPAP, 85, 186 and 190 after s.c. injection of 5 mg/kg in rats

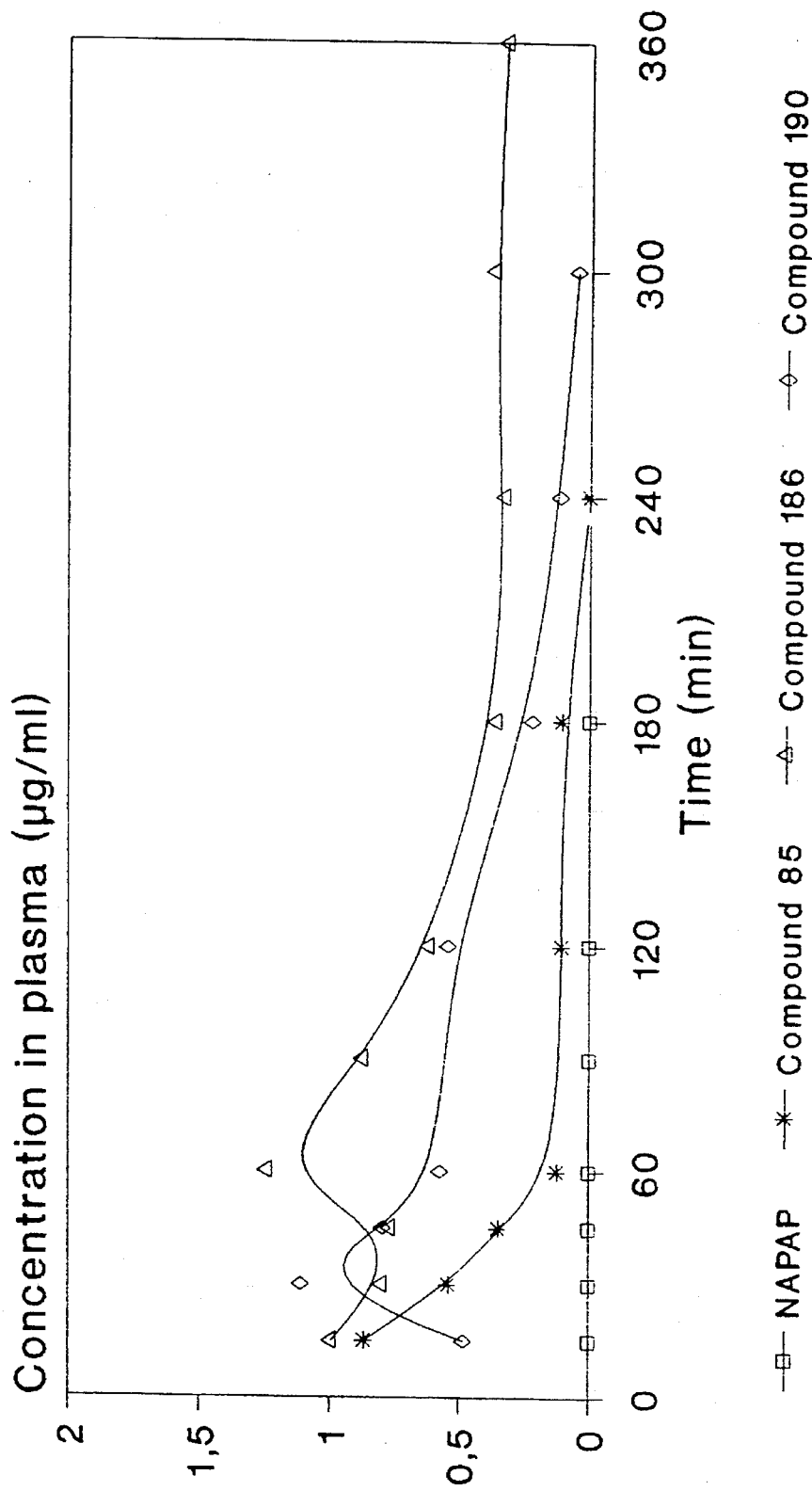
Fig. 3 Plasma levels of NAPAP, 85, 186 and 190 after p.o. administration of 100 mg/kg in rats

META-SUBSTITUTED PHENYLALANINE DERIVATIVES

The present invention relates to new proteinase inhibitors which contain a phenylalanine residue which carries a substitution on its phenyl ring. Variation of the substituent on the phenyl ring and in particular the introduction of hydrophobically substituted secondary amino acids led to the discovery of inhibitors showing improved bioavailability.

Proteinase inhibitors are potential drugs which can be used to control physiological processes induced and maintained by proteinases. For many endogenous and naturally occurring inhibitors, respectively, it has been shown that they can influence the activity of proteinases in vivo and alleviate hyperproteolytic states [see Hörl, W. H. In: Design of Enzyme Inhibitors as Drugs, p. 573–581, (Sandler, M. and Smith, H. J., Eds.) Oxford, New York, Tokyo: Oxford University Press, 1989]. However, the therapeutic application of such inhibitors of relatively high molecular weight is limited due to their particular protein structure. As these inhibitors are not absorbed in the intestine upon oral administration on the one hand and exert an antigenic activity on the other hand, it was of great interest to search for synthetic enzyme inhibitors of low molecular weight.

The four classes of enzymes which are responsible for proteinase-dependent processes comprise the serine, thiol, metallo, and aspartate proteinases. Serine proteinases are proteolytic enzymes which possess a reactive serine residue in the active center. Enzymes which, such as trypsin, split off C-terminal peptide bonds of the basic amino acids arginine and lysine, belong to the trypsin family of the serine proteinases. In this group, those enzymes which participate in the defense systems of blood are of particular physiological significance. Particularly, they are the enzymes of the coagulation system, but also those which induce fibrinolysis, release kinin and produce the complement activation or those which themselves are components of the mentioned enzyme systems.

Blood coagulation is triggered by zymogen activation via two different pathways. The first, intrinsic pathway leads to blood coagulation via a chain of reactions mediated by blood constituents. The second, extrinsic pathway leads to coagulation via a shorter chain of reactions based on an interaction between blood and tissue constituents. Both ways produce the activation of the zymogen factor X into the serine proteinase factor $X_a$ which itself catalyzes the activation of prothrombin into the fibrinogen-coagulating serine proteinase, thrombin. Being a common product of the intrinsic as well as of the extrinsic activation pathway, factor $X_a$ appears to be a preferential target enzyme for inhibitory intervention in the blood coagulation process.

For the development of synthetic inhibitors for trypsin-like serine proteinases, benzamidine derivatives have been extensively investigated (J. Stürzebecher et al., Acta Biol. Med. Germ. 35, 1665–1676, 1976). Among them, amino acid derivatives containing a benzamidine moiety proved to be particularly favorable core structures (G. Wagner et al., Pharmazie 56, 597–603, 1981 and J. Stürzebecher et al., ibid, 639–641; UK Patent Application 2 007 663 A). Among these compounds, phenylalanine derivatives with a meta-oriented amidino group are selective factor $X_a$ inhibitors while analogous compounds with a para-oriented amidino group are the core structures for the development of selective thrombin inhibitors.

Nα-tosylglycyl-3-amidinophenylalanine methyl ester (TAPAM; $K_i=8.4\times10^{-7}$ mole/l) has been proposed as a selective factor $X_a$-inhibiting amino acid derivative containing a benzamidine moiety and a meta-oriented amidino group (J. Stürzebecher et al., Thromb. Res. 54, 245–252, 1989). The most efficient thrombin inhibitor is the phenylalanine derivative Nα-(2-naphthylsulfonylglycyl)-4-amidinophenylalanine piperidide ($K_i=6\times10^{-9}$ mole/l) with a para-oriented amidino group which is designated as NAPAP (J. Stürzebecher et al., Thromb. Res. 29, 635–642, 1983).

Other types of selective inhibitors of factor $X_a$ and thrombin, as well, are known: the first group is comprised of the peptidyl-arginine-chloromethyl ketones, e.g. Ile-Glu-Gly-Arg-$CH_2Cl$ which inhibits factor $X_a$ (C. Kettner et al., Thromb. Res. 22, 645–652, 1981), or H-D-Phe-Pro-Arg-$CH_2Cl$ which selectively inhibits thrombin (C. Kettner et al., Thromb. Res. 14, 969–973, 1979). A second group is comprised of the peptidylarginine aldehydes, e.g. Ile-Glu-Gly-Arg-H (S. Bajusz, Folia Haematol. 109, 16–21, 1982) and H-D-Phe-Pro-Arg-H (S. Bajusz, Int. J. Peptide Protein Res. 12, 217–221, 1978), which inhibit factor $X_a$ and thrombin, respectively. However, these inhibitors are relatively unstable and may cause undesired side reactions due to their reactive capacity. Further, selective thrombin inhibitors have been described: (2R,4R)-4-methyl-1-[Nα-(3-methyl-1,2,3,5-tetrahydro-8-quinolinesulfonyl)-L-arginine]-2-pipecoline-carboxylic acid (R. Kikumoto et al., Biochemistry 23, 85–90, 1984) and the boronic acid derivative BOC-D-Phe-Pro-Boro-Arg-$C_{10}H_{16}$ (see European Patent Application No. 0 293 881).

As therapeutically applicable, non-selective inhibitors of thrombin and of the plasma clotting factors $X_a$ and $XII_a$ as well as of kallikreins, enzymatic complement factors and trypsin, the methanesulfonic acid salt of the 4-(6-guanidinohexanoyloxy)-benzoic acid ethyl ester (M. Muramatu et al., Biochim. Biophys. Acta 268, 221–224, 1972) and the dimethanesulfonic acid salt of the 6-amidino-2-naphthyl-p-guanidinobenzoic acid (see US Patent No. 4 454 338) have been described.

The anticoagulant and antithrombotic effects have been shown in vivo for all the mentioned inhibitors, whereas absorption after oral administration has so far only been observed for the aldehyde N-methyl-D-Phe-Pro-Arg-H (Bagdy et al., Thromb. Haemostas. 62, 535, 1989) and the boronic acid derivative BOC-D-Phe-Pro-Boro-Arg-$C_{10}H_{16}$ (see European Patent Application No. 0 293 881).

The until now investigated thrombin inhibitors of the benzamidine type possess pharmacodynamic and pharmacokinetic properties which make them unfavorable for a therapeutic application. Their toxicity is relatively high with an $LD_{50}$ ranging from 10 to 50 mg/kg (B. Kaiser et al., Pharmazie 42, 119–121, 1987). The compounds are more quickly excreted from the circulatory system than, e.g., the arginine derivative (2R,4R)-4-methyl-1-[Nα-(3-methyl-1,2,3,5-tetrahydro-8-quinolinesulfonyl)-L-arginine]-2-pipecoline-carboxylic acid and the boronic acid derivative BOC-D-Phe-Pro-Boro-Arg-$C_{10}H_{16}$, respectively (J. Hauptmann et al., Pharmazie 46, 57–58, 1991). Upon oral application they are not absorbed in the intestine (B. Kaiser et al., Biomed. Biochim. Acta 44, 1201–1210, 1985). The responsibility for the inadequate pharmacological properties is probably attributable to the reduction in hydrophobicity caused by the highly basic amidino function (B. Kaiser et al., Pharmazie 42, 119–121, 1987). Experiments aimed at replacing the strongly basic amidino function in highly effective inhibitors by less basic groups failed; such modifications resulted in a significant loss in efficacy (J. Stürzebecher et al., Pharmazie 43, 782–783, 1988).

Accordingly, therapeutically applicable inhibitors of clotting factors with excellent pharmacological properties have been designed and synthesized. For this purpose, we started from phenylalanine derivatives with a meta-oriented amidino group which have been proven to be selective factor $X_a$ inhibitors (J. Stürzebecher et al, Thromb Res. 54 245–252, 1989). Based on the knowledge that an increase in hydrophobicity could cause a modification of the pharmacological properties, new inhibitor core structures could be found after reaching anti-factor $X_a$ activity. Therefore, the basic amidino group has been modified and hydrophobically substituted secondary amino acids have been introduced, respectively. The compound Nα-2-naphthylsulfonyl-3-amidinophenylalanyl proline, for example, has been synthesized within this framework. It has been found, contrary to our expectations, that this compound does not selectively inhibit factor $X_a$, but surprisingly inhibits thrombin. Furthermore, it has been observed that this compound possesses excellent pharmacokinetic properties. After subcutaneous application in rats, a relatively high blood level is reached which is maintained in an anticoagulantly effective concentration for a prolonged period of time. After oral administration to rats, the compound is absorbed by the intestine. This also applies to analogous compounds in which the amidino group has been modified, e.g. in derivatives having an oxamidino group. The new derivatives are also characterized by a reduced toxicity.

Such directly efficient inhibitors are thus appropriate as anticoagulants in various types of application.

The present invention relates to new proteinase-inhibiting D,L-, L- and D-phenylalanine derivatives of formula I

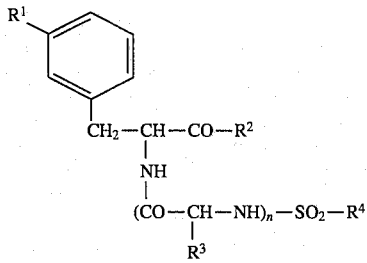

wherein
R¹ represents a basic group of formula

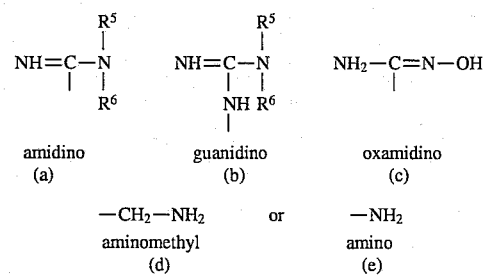

$R^5$ and $R^6$ in formulas (a) and (b) designating hydrogen or a straight or branched low alkyl residue, R² represents
(f) OH, O-alkyl, O-cycloalkyl, O-aralkyl, n=0,
(g) a group of formula

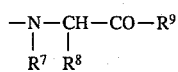

wherein R⁷ represents hydrogen or a straight or branched low alkyl residue and R⁸ represents a straight or branched low alkyl residue, a 1- or 2-hydroxyethyl residue, a methylmercaptoethyl residue, an aminobutyl residue, a guanidinopropyl residue, a carboxy(low)alkyl residue, a carboxamido(low)alkyl residue, a phenyl(low)alkyl residue, the ring of which may be substituted with OH, halogen, low alkyl or methoxy, a cyclohexyl or cyclohexylmethyl residue, the ring of which may be substituted with OH, halogen, low alkyl or methoxy, or an N-heteroaryl(low)alkyl residue having 3 to 8 carbon atoms in the heteroaryl, e.g. imidazolylmethyl or indolylmethyl, the group (e) having a racemic, or D or L configuration, respectively,
(h) a group of formula.

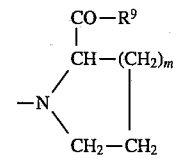

wherein m represents the number 1 or 2, and wherein one of the methylene groups may be substituted with a hydroxyl, carboxyl, low alkyl or aralkyl residue, the group (h) having a racemic, or D or L configuration, respectively,
(i) a group of formula

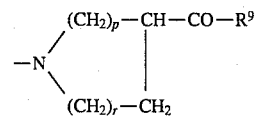

wherein p=r=1, p=1 and r=2 or p=2 and r=1 and wherein one of the methylene groups may be substituted with a hydroxyl, carboxyl, low alkyl or aralkyl residue,
(k) a piperidyl group, which may be substituted with a low alkyl or hydroxyl residue in one of the positions 2, 3 and 4, wherein a further aromatic or cycloaliphatic ring, preferentially phenyl or cyclohexyl, may be condensed on the heterocycloaliphatic rings of formulas (h), (i), (k) in position 2,3 or 3,4, related to the heteroatom,
(l) a piperazyl group, which may be substituted in p position with a low alkyl residue, an aryl residue or an alkoxycarbonyl residue,
(m) a group of formula

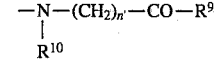

wherein n' represents the numbers 1 to 6 and $R^{10}$ represents hydrogen or the methyl or cyclohexyl residue,
(n) a group of formula

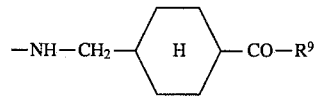

wherein $R^9$ in formulas (g), (h), (i), (l), (m) and (n) designates a hydroxyl, straight or branched low alkoxy or a benzyloxy group, or
(o) a combination of 2 to 20, preferentially 2 to 5, in particular 2 or 3, of the residues linked through amide bonds and derived from the groups defined under (g), (h), (i), (k), (l), (m) and (n) ($R^9$=single bond), the C-terminal residue being possibly bound with a residue $R^9$, $R^3$ represents hydrogen or a straight or branched low alkyl or a 1- or 2-hydroxyethyl residue, wherein n designates the number 0 or 1, and $R^4$ represents an aryl residue, e.g. phenyl, methylphenyl, α- or β-naphthyl or 5-(dimethylamino)-naphthyl, or a heteroaryl residue, e.g. quinolyl, wherein low means 1–4 carbon atoms, and the salts thereof with mineral or organic acids.

Among the phenylalanine derivatives defined in the general claims, those compounds wherein $R^1$ represents a basic group of formula (a)=amidino, (b)=guanidino, (c)=oxamidino, (d)=aminomethyl or (e)=amino, $R^2$ represents O-alkyl, O-cycloalkyl or aralkyl and n=0, or a heterocycloaliphatic residue as more precisely defined in formulas (h), (i), (k) and (l), $R^9$ in formulas (h) and (i) being possibly a hydroxyl, straight or branched low alkoxy, cycloalkoxy or aralkoxy group, $R^4$ represents an aryl or heteroaryl residue, preferentially β-naphthyl, and n represents the number 0, are of particular significance.

Compounds of general formula I wherein $R^1$=amidino (a) can be synthesized according to the known methods described hereinafter.

3-Cyanobenzyl-dialkyl-acylamido-malonates of general formula II

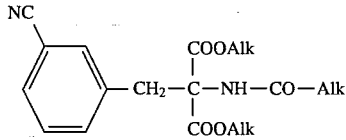

wherein Alk preferentially means —CH$_3$ or —C$_2$H$_5$, are converted into 3-cyanophenylalanine III

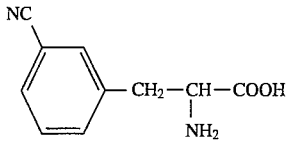

in a mixture of 3N HCl and acetic acid by heating under reflux.

By sulfonylation of compounds of structure III with an aryl or heteroarylsulfonyl chloride, respectively, or acylation with a sulfonylated amino acid halide in the presence of a base, compounds of general formula IV

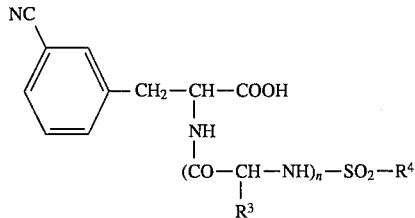

are obtained, wherein n=0 or 1, and $R^3$ and $R^4$ have the denorations given in general formula I.

Compounds of general formula V

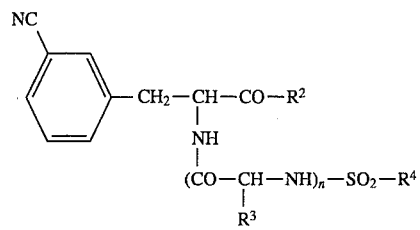

wherein $R^2$ has the denorations mentioned in general formula I under (g), (h), (i), (k), (l), (m), (n) and (o), $R^3$ and $R^4$ have the denorations mentioned in this formula, and $R^9$ represents a straight or branched alkoxy or benzyloxy group, respectively, are represented according to the first coupling procedure by coupling of compounds of structure IV with a corresponding amino carboxylate according to the mixed anhydride procedure, whereby compounds of structure IV are preferentially reacted with isobutyl chloroformate in the presence of an adequate tertiary base, e.g. 4-methylmorpholine, at −15° to −20° C. in an aprotic solvent and finally converted with an amino carboxylate or an amine.

According to a second coupling procedure, compounds of general formula IV are coupled according to the DCC procedure with corresponding amino carboxylates, whereby the compounds of structure IV are reacted with an adequate aprotic solvent with dicyclohexylcarbodiimide in the presence of 1-hydroxybenzotriazole and converted into compounds of structure V with the cited amino carboxylates or amines.

According to a third coupling method, compounds of structure IV are isolated after transformation into active esters with e.g. N-hydroxysuccinimide, 2,3,4,5,6,-pentafluorophenol or p-nitrophenol in the presence of dicyclohexylcarbodiimide, or converted without intermediate isolation into compounds of the general formula V with corresponding amino carboxylates or amines.

According to a fourth coupling method, compounds of structure IV, wherein n=0, are transformed with e.g. thionyl chloride into acid chlorides which are finally converted into compounds of the general formula V with corresponding amino carboxylates or amines.

By a mild alkaline or acidic hydrolysis of compounds of structure V with e.g. dilute NaOH or trifluoracetic acid, compounds having the carboxylic acid structure of general formula V are obtained, wherein $R^2$, $R^3$ and $R^4$ are denoted as mentioned in general formula I and wherein $R^9$ defined in $R^2$=OH.

Starting from compounds having the carboxylic acid structure V, further amino acids can be coupled according to the previously described methods.

By addition of H$_2$S to V having a carboxylic acid or carboxylate structure in pyridine in the presence of triethylamine, thioamides of general formula VI

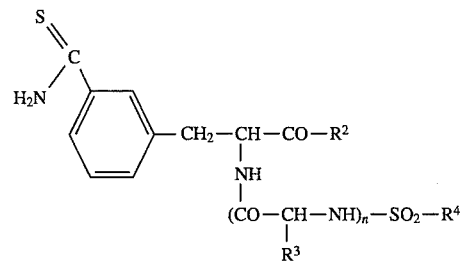

are obtained, wherein the denorations of the substituents $R^2$, $R^3$ and $R^4$ correspond to those of the general formula I.

By conversion of compounds of structure VI with an alkyl halide, preferentially methyl iodide, the thioimide carboxylate halides VII

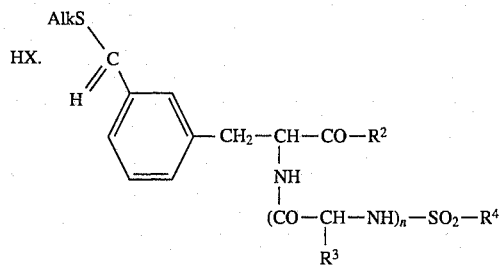

are obtained. The denotations of n and $R^2$ to $R^4$ correspond to those of general formula I, Alk represents low alkyl, preferentially —$CH_3$, and X means halogen, in general, iodine.

Moreover, compounds of structure V with a low alcohol, possibly in the presence of a solvent such as dioxane or chloroform, in the presence of an anhydrous hydrogen halide, can be converted into the imide carboxylate halides VIII

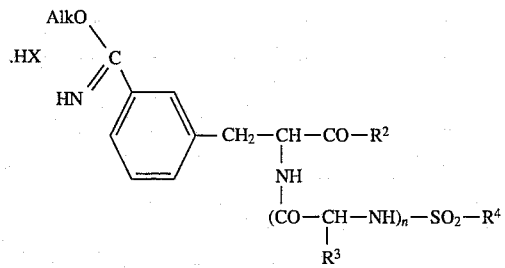

whereby the compounds having a free —COOH group are simultaneously esterified with the alcohol used. The denotations of n and $R^2$ to $R^4$ correspond to those of general formula I, Alk represents low alkyl, preferentially —$CH_3$ or —$C_2H_5$, and X means halogen, in general, chlorine.

To represent the target compounds IX,

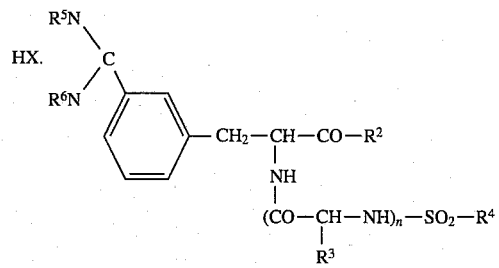

wherein n=0 or 1, the denotations of the substituents $R^1$ to $R^6$ being analogous to those of general formula I and X=halogen, the thioimide carboxylate salts of general formula VII are converted into compounds of general formula IX in an alcoholic solution with ammonium acetate or an alkyl ammonium acetate, respectively, or the imide carboxylate salts (VIII) are converted into compounds of general structure IX in an alcoholic ammonia solution.

Compounds of general formula IX having a t-butoxy residue ($R^9$) in the substituent $R^2$ can further be transformed through hydrolysis with trifluoracetic acid into compounds of structure IX having a carboxylic acid structure ($R^9$=OH).

Compounds of general formula IX having an OH group ($R^2$ or $R^9$) can thereafter be transformed into compounds of general formula IX having a carboxylate structure ($R^2$, $R^9$=O-alkyl, O-cycloalkyl, O-aralkyl) with preferentially low aliphatic ($C_1$–$C_8$), cycloaliphatic or aralaliphatic alcohols, in the presence of hydrochloric acid or p-toluenesulfonic acid.

Compounds of general formula I wherein $R^1$=oxamidino (c) are synthesized in the same manner as compounds wherein $R^1$=amidino (a) via the intermediate products of general formulas II to VII. In the last step of synthesis, the thioimide carboxylate salts (VII) are converted with hydroxylammonium acetate into compounds of general formula I wherein $R^1$ represents the oxamidino group (c).

Compounds of general formula I wherein $R^1$=aminomethyl (d) are also synthesized in this way via the intermediate products of general formulas II to V. In order to obtain the target compounds of general formula I wherein $R^1$=—$CH_2$—$NH_2$, the cyano compounds (V) are catalytically reduced to aminomethyl compounds with e.g. Raney-Nickel/hydrogen in an alcoholic solution in the presence of ammonia. The free bases obtained are transformed into salts, preferentially hydrochlorides, in an appropriate way.

In principle, compounds of general formula I wherein $R^1$=guanidino (b) can be represented according to the same outline of synthesis as those having an amidino structure (a).

For that purpose, 3-nitrobenzyl-dialkyl-acylamidomalonates of general formula X,

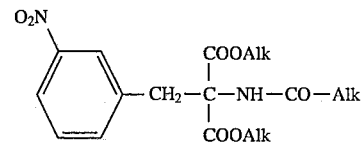

wherein Alk preferentially means —$CH_3$ or —$C_2H_5$, are converted into 3-nitrophenylalanine (XI)

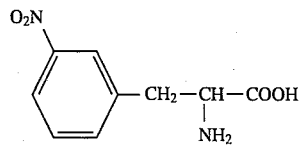

by heating under reflux in a mixture of 3N HCl and acetic acid.

Compounds XII and XIII

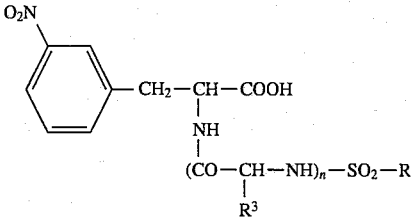

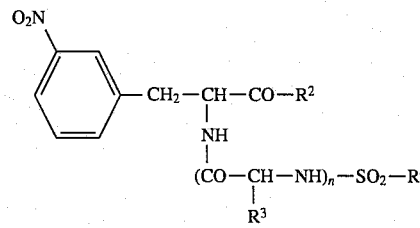

are obtained in the same way as the corresponding cyano compounds IV and V, the denotations of n, $R^2$, and $R^3$ and $R^4$ being the same.

By catalytic hydrogenation by means of e.g. Raney Nickel/hydrogen in an adequate solvent, the amino compounds of general formula XIV

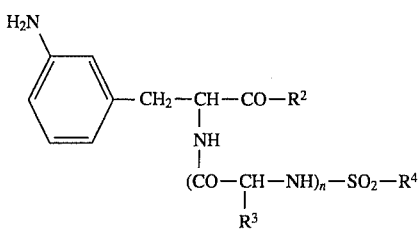

$$\text{XIV}$$

are obtained from structure XIII; these compounds are converted into the guanidino compounds of general formula I wherein $R^1$=guanidino (b) by means of an adequate guanylation reagent, e.g. 1-amidino-3,5-dimethyl-pyrazole nitrate.

Compounds having the general formula I wherein $R^1$=guanidino (b), oxamidino (c), aminomethyl (d) or amino (e), respectively, and with a t-butoxy residue ($R^9$) in the substituent $R^2$ can, by hydrolysis with trifluoroacetic acid, be transformed into compounds having a carboxylic acid structure ($R^9$=OH) which can then be converted into compounds having a carboxylate structure ($R^9$=alkoxy) by esterification with lower alcohols, preferentially methanol, in the presence of hydrochloric acid or p-toluenesulfonic acid.

The biological activity of the compounds of the present invention was determined in vitro as well as in vivo. For characterizing the inhibitory activity in vitro, the dissociation constants $K_i$ for the inhibition of trypsin and the related enzymes thrombin, plasmin, factor $X_a$, tPA, glandular kallikrein, factor $XII_a$ and plasma kallikrein, respectively, were calculated according to the formula $$K_i = \frac{[E] \cdot [I]}{[EI]}$$

wherein [E] represents the concentration in free enzyme, [I] the concentration in free inhibitor and [EI] the concentration in enzyme-inhibitor complex (Dixon, Biochem. J. 55, 170–173, 1953). The smaller the $K_i$-value for a tested enzyme, the higher the affinity of the inhibitor for the enzyme and the smaller the quantity of inhibitor needed for the inhibition of the enzyme, e.g. thrombin.

Various coagulation tests were used in vitro to determine the efficacy of the inhibitors towards the thrombin-induced coagulation of its natural substrate fibrinogen. For that purpose, the thrombin time (TT), the activated partial thromboplastin time (aPTT) and the prothrombin time (PT, Quick value) were determined in human plasma.

The toxicity of the compounds of the present invention was evaluated by determination of the $LD_{50}$ (=dose that causes the death of 50% of the test animals within an observation time of one week) in the mouse after intravenous and peroral administration, respectively.

For the pharmacokinetic characterization, the plasma concentration of selected derivatives was determined in rats after intravenous (i.v.), subcutaneous (s.c.) and peroral (p.o.) application according to the following three-step procedure:

1. A physiological NaCl solution of the substance to be tested was submitted to high pressure liquid chromatography (HPLC) in order to determine its characteristic substance-specific retention time with the chosen test conditions.
2. The substance to be tested was diluted in vitro in rat plasma. This solution was also submitted to HPLC to see whether the characteristic peak of the substance once again appeared at the substance-specific retention time.
3. The substance to be tested was dissolved in physiological NaCl solution and administered i.v., s.c. and p.o. to rats in doses of 1, 5 and 100 mg per kg body weight, respectively. Blood samples were taken at time intervals of 15 minutes, from which plasma samples were prepared by centrifugation; those samples were also submitted to HPLC to see whether the characteristic peak of the substance appeared again at the substance-specific retention time.

To demonstrate the pharmacological efficacy, the substance to be tested was dissolved in physiological NaCl solution and administered i.v., s.c. and p.o. to rats in doses of 1, 5 and 100 mg per kg body weight, respectively. Blood samples were taken at time intervals of 15 minutes, from which plasma samples were prepared by centrifugation and investigated in the coagulation test (thrombin-induced plasma coagulation).

As examples of general formula I with meta-oriented basic groups, the following compounds can be cited:
Compounds wherein $R^1$=amidino (a):
N-α-(2-Naphthylsulfonyl)-3-amidino-(D,L)-phenylalanine-n-hexyl-, -cyclohexyl- and -n-octyl ester
N-α-(2-Naphthylsulfonyl)-3-amidino-(D,L)-phenylalanine-4-hydroxypiperidide
N-α-(2-Naphthylsulfonyl)-3-amidino-(D)-phenylalanyl-(D)-proline and -methyl ester
N-α-(2-Naphthylsulfonyl)-3-amidino-(L)-phenylalanyl-(L)-proline and -methyl ester
N-α-(2-Naphthylsulfonyl)-3-amidino-(D)-phenylalanyl-(L)-proline and -methyl ester
N-α-(2-Naphthylsulfonyl)-3-amidino-(D,L)-phenylalanyl-(D,L)-proline and -methyl ester
N-α-(2-Naphthylsulfonyl)-3-amidino-(D,L)-phenylalanyl-(L)- 4-hydroxyproline and -methyl ester
N-α-(2-Naphthylsulfonyl)-3-amidino-(D,L)-phenylalanyl-(D,L)-prolyl- 4-aminobutyric acid and -methyl butyrate
N-α-(2-Naphthylsulfonyl)-3-amidino-(L)-phenylalanyl-methyl-(L)-pipecolinate
N-α-(2-Naphthylsulfonyl)-3-amidino-(L)-phenylalanyl-methyl-(D)-pipecolinate
N-α-(2-Naphthylsulfonyl)-3-amidino-(D,L)-phenylalanyl-ethyl-, -n-butyl-, -n-hexyl- and -cyclohexyl-(D,L)-pipecolinate
N-α-(2-Naphthylsulfonyl)-3-amidino-(D,L)-phenylalanyl-(D,L)-pipecolyl- 4-aminobutyric acid
N-α-(2-Naphthylsulfonyl)-3-amidino-(D,L)-phenylalanyl-(D,L)-pipecolyl- 6-aminocaproic acid
N-α-(2-Naphthylsulfonyl)-3-amidino-(D,L)-phenylalanyl-(D,L)-pipecolyl-glycyl-glycine
N-α-(2-Naphthylsulfonyl)-3-amidino-(D,L)-phenylalanyl-(D,L)-pipecolyl-glycyl-(D,L)-pipecolic acid
N-α-(2-Naphthylsulfonyl)-3-amidino-(D,L)-phenylalanyl-(D,L)-pipecolyl-glycyl-glycyl-(D,L)-pipecolic acid
N-α-(2-Naphthylsulfonyl)-3-amidino-(D,L)-phenylalanyl-(D,L)-pipecolyl- 6-aminocaproyl-(D,L)-pipecolic acid
N-α-(2-Naphthylsulfonyl)-3-amidino-(D,L)-phenylalanyl-ethyl-, -n-butyl-, -n-hexyl- and -cyclohexyl nipecotate
N-α-(2-Naphthylsulfonyl)-3-amidino-(D,L)-phenylalanyl-ethyl-, -n-butyl-, -n-hexyl- and -cyclohexyl isonipecotate
N-α-(2-Naphthylsulfonyl)-3-amidino-(D,L)-phenylalanyl-4-aminobutyric acid and -methyl butyrate
N-α-(2-Naphthylsulfonyl)-3-amidino-(D,L)-phenylalanyl-6-aminocaproic acid and -methyl caproate
N-α-(2-Naphthylsulfonyl)-3-amidino-(D,L)-phenylalanyl-cyclohexyl-β -alanine and -methyl ester
N-α-(2-Naphthylsulfonyl)-3-amidino-(D,L)-phenylalanyl-4-aminomethyl-cyclohexanecarboxylic acid and -methyl cyclohexanecarboxylate
N-α-(2-Naphthylsulfonyl)-3-amidino-(D,L)-phenylalanyl-3-carboxy-(D,L)-phenylalanine N-α-(2-Naphthylsulfonyl)-3-amidino-(D,L)-phenylalanyl-3-methoxycarbonyl-(D,L)-phenylalanine methyl ester N-α-(2-Naphthylsulfonyl)-3-amidino-(D,L)-phenylalanyl-(D,L)-homophenylalanine and -methyl ester N-α-(2-Naphthylsulfonyl)-3-amidino-(D,L)-phenylalanyl-4-aminobutyryl-glycine and -methyl ester Compounds wherein $R^1$=guanidino (b):

N-α-(2-Naphthylsulfonyl)-3-guanidino-(D,L)-phenylalanine-methyl-, -n-butyl-, -n-hexyl- and -cyclohexyl ester N-α-(2-Naphthylsulfonyl)-3-guanidino-(D,L)-phenylalanine-4-methylpiperidide N-α-(2-Naphthylsulfonyl)-3-guanidino-(D,L)-phenylalanine-N-methylpiperazide N-α-(2-Naphthylsulfonyl)-3-guanidino-(D,L)-phenylalanine-N-phenylpiperazide N-α-(2-Naphthylsulfonyl)-3-guanidino-(D,L)-phenylalanine-N-ethoxycarbonylpiperazide N-α-(2-Naphthylsulfonyl)-3-guanidino-(D,L)-phenylalanyl-(D,L)-proline and -methyl ester N-α-(2-Naphthylsulfonyl)-3-guanidino-(D,L)-phenylalanyl-(D,L)-pipecolic acid, -methyl- and -n-butyl pipecolinate N-α-(2-Naphthylsulfonyl)-3-guanidino-(D,L)-phenylalanyl-isonipecotic acid, -methyl- and -n-butyl isonipecotate N-α-(2-Naphthylsulfonyl)-3-guanidino-(D,L)-phenylalanyl-4-methyl-(D,L)-pipecolic acid, -methyl- and -n-butyl pipecolinate N-α-(2-Naphthylsulfonyl)-3-guanidino-(D,L)-phenylalanyl-2-methyl-nipecotic acid, -methyl- and -n-butyl nipecotate N-α-(2-Naphthylsulfonyl)-3-guanidino-(D,L)-phenylalanyl-1,2,3,4-tetrahydroisoquinoline-3-carboxylic acid and -methyl ester N-α-(2-Naphthylsulfonyl)-3-guanidino-(D,L)-phenylalanyl-decahydroquinoline-4-carboxylic acid and -methyl ester Compounds wherein $R^1$=oxamidino (c):

N-α-(2-Naphthylsulfonyl)-3-oxamidino-(D,L)-phenylalanine-methyl-, -n-butyl-, -n-hexyl- and -cyclohexyl ester N-α-(2-Naphthylsulfonyl)-3-oxamidino-(D,L)-phenylalanine-N-methylpiperazide N-α-(2-Naphthylsulfonyl)-3-oxamidino-(D,L)-phenylalanine-N-phenylpiperazide N-α-(2-Naphthylsulfonyl)-3-oxamidino-(D,L)-phenylalanine-N-ethoxycarbonylpiperazide N-α-(2-Naphthylsulfonyl)-3-oxamidino-(D,L)-phenylalanyl-(D,L)-proline and -methyl ester N-α-(2-Naphthylsulfonyl)-3-oxamidino-(D,L)-phenylalanyl-(D,L)-pipecolic acid methyl- and -n-butyl pipecolinate N-α-(2-Naphthylsulfonyl)-3-oxamidino-(D,L)-phenylalanyl-isonipecotic acid methyl- and -n-butyl isonipecotate N-α-(2-Naphthylsulfonyl)-3-oxamidino-(D,L)-phenylalanyl-4-methyl-(D,L)-pipecolic acid, -methyl- and -n-butyl pipecolinate N-α-(2-Naphthylsulfonyl)-3-oxamidino-(D,L)-phenylalanyl-2-methyl-nipecotic acid, -methyl- and -n-butyl 2-methyl-nipecotate N-α-(2-Naphthylsulfonyl)-3-oxamidino-(D,L)-phenylalanyl-1,2,3,4-tetrahydroisoquinoline-3-carboxylic acid methyl ester N-α-(2-Naphthylsulfonyl)-3-oxamidino-(D,L)-phenylalanyl-decahydroquinoline-4-carboxylic acid and -methyl ester Compounds wherein $R^1$=aminomethyl (d):

N-α-(2-Naphthylsulfonyl)-3-aminomethyl-(D,L)-phenylalanine-methyl-, -n-butyl-, -n-hexyl- and -cyclohexyl ester N-α-(2-Naphthylsulfonyl)-3-aminomethyl-(D,L)-phenylalanine-N-methylpiperazide N-α-(2-Naphthylsulfonyl)-3-aminomethyl-(D,L)-phenylalanine-N-phenylpiperazide N-α-(2-Naphthylsulfonyl)-3-aminomethyl-(D,L)-phenylalanine-N-ethoxycarbonylpiperazide N-α-(2-Naphthylsulfonyl)-3-aminomethyl-(D,L)-phenylalanyl-(D,L)-proline and -methyl ester N-α-(2-Naphthylsulfonyl)-3-aminomethyl-(D,L)-phenylalanyl-(D,L)-n-butyl pipecolinate N-α-(2-Naphthylsulfonyl)-3-aminomethyl-(D,L)-phenylalanyl-n-butyl isonipecotate N-α-(2-Naphthylsulfonyl)-3-aminomethyl-(D,L)-phenylalanyl-4-methyl-(D,L)-pipecolic acid, -methyl- and -n-butyl pipecolinate N-α-(2-Naphthylsulfonyl)-3-aminomethyl-(D,L)-phenylalanyl-2-methyl-nipecotic acid, -methyl- and -n-butyl 2-methyl-nipecotate N-α-(2-Naphthylsulfonyl)-3-aminomethyl-(D,L)-phenylalanyl-1,2,3,4-tetrahydroisoquinoline-3-carboxylic acid and -methyl ester N-α-(2-Naphthylsulfonyl)-3-aminomethyl-(D,L)-phenylalanyl-decahydroquinoline-4-carboxylic acid and -methyl ester Compounds wherein $R^1$=amino (e):

N-α-(2-Naphthylsulfonyl)-3-amino-(D,L)-phenylalanine-methyl-, -n-butyl-, -n-hexyl- and -cyclohexyl ester N-α-(2-Naphthylsulfonyl)-3-amino-(D,L)-phenylalanine-N-methylpiperazide N-α-(2-Naphthylsulfonyl)-3-amino-(D,L)-phenylalanine-N-phenylpiperazide N-α-(2-Naphthylsulfonyl)-3-amino-(D,L)-phenylalanine-N-ethoxycarbonylpiperazide N-α-(2-Naphthylsulfonyl)-3-amino-(D,L)-phenylalanyl-(D,L)-proline and -methyl ester N-α-(2-Naphthylsulfonyl)-3-amino-(D,L)-phenylalanyl-(D,L)-pipecolic acid methyl- and -n-butyl pipecolinate N-α-(2-Naphthylsulfonyl)-3-amino-(D,L)-phenylalanyl-isonipecotic acid methyl- and -n-butyl isonipecotate N-α-(2-Naphthylsulfonyl)-3-amino-(D,L)-phenylalanyl-4-methyl-(D,L)-pipecolic acid, -methyl- and -n-butyl pipecolinate N-α-(2-Naphthylsulfonyl)-3-amino-(D,L)-phenylalanyl-2-methyl-nipecotic acid, -methyl- and -n-butyl 2-methyl-nipecotate N-α-(2-Naphthylsulfonyl)-3-amino-(D,L)-phenylalanyl-1,2,3,4-tetrahydroisoquinoline-3-carboxylic acid methyl ester N-α-(2-Naphthylsulfonyl)-3-amino-(D,L)-phenylalanyl-decahydroquinoline-4-carboxylic acid and -methyl ester The compounds indicated as racemates can be available after corresponding separation as pure enantiomers or diastereomers.

The invention is explained in detail in the examples described hereafter. For abbreviations used in the examples, the following legend is to be referred to.

| LEGEND TO TABLES 1–18 AND LIST OF ANALYTICAL DATA | |
|---|---|
| No | Number of compound |
| SC | Starting compound |
| $R^1$, $R^2$, $R^4$ | Substituents in formula I |
| n | n in formula I |
| Y (%) | Yield in % |
| mp (°C.) | Melting point in °C. |
| dec | Decomposition |

13
-continued

| | LEGEND TO TABLES 1–18 AND LIST OF ANALYTICAL DATA |
|---|---|
| Pu | Purification, either through crystallization (CR) or column chromatography (CC) |
| HX | Salt form, either hydrochloride (HCl) or hydroiodide (HI) |
| P | Procedure, either A or B |
| TLC | Thin-layer chromatography |
| SS | Solvent system (see below) |
| $R_f$ | Retention factor, when 2 $R_f$-values are indicated, double spot formation due to isomerism |

Thin-layer chromatography was performed on MERCK thin-layer plates pre-coated with silica gel 60, F 254, using the following solvent systems (SS):

SS 1: organic phase of ethyl acetate/acetic acid/water (4/1/½)

SS 2: chloroform/methanol (19/1)

SS 3: chloroform/methanol/acetic acid (40/4/1)

SS 4: toluene/acetone/methanol (7/2/1)

Spray reagents: ninhydrin—for primary and secondary aliphatic amino groups 4-dimethylaminobenzaldehyde—for primary aromatic amino groups Sakaguchi—for guanidino groups To purify the crude products, column chromatography was carried out using silica gel 60 with a grain size of 0.035 to 0.070 mm.

| ABBREVIATIONS used in examples 1–18 | |
|---|---|
| TEA | triethylamine |
| HOBT | 1-hydroxybenzotriazole |
| DCC | dicyclohexylcarbodiimide |
| IBCF | isobutyl chloroformate |
| NMM | 4-methylmorpholine |
| DMF | dimethylformamide |
| THF | tetrahydrofuran |
| TFA | trifluoracetic acid |
| Pd/C | palladium on activated charcoal |
| TLC | thin-layer chromatography |

EXAMPLE 1

N-α-(2-Naphthylsulfonyl)-3-amidino-(D,L)-phenylalanine and -ester (6–11, Table 1).

(3-Cyanobenzyl)-diethyl-acetamido-malonate (1)

10.0 g of 3-cyanobenzyl bromide and 11.0 g of diethyl-acetamido-malonate were dissolved in 100 ml of abs. dioxane. To this solution a solution of 1.15 g of sodium in 50 ml of abs. ethanol was added with stirring. The reaction mixture was heated for 5 hours in a boiling water bath. The solvent was then evaporated under reduced pressure, whereupon the residue was taken up in chloroform and the solution was washed with dilute NaOH, HCl and finally with water. The organic phase was dried-over $MgSO_4$. The solvent was removed by distillation under reduced pressure and the residue crystallized from methanol/water. Yield: 80%, mp 143°–145° C.

14

3-cyano-(D,L)-phenylalanine (2)

12.0 g of compound 1 were heated under reflux in a mixture of 32 ml of acetic acid and 64 ml of 3N HCl for 6 hours. The solvent was then removed by evaporation under reduced pressure and the residue dried. The obtained product was dissolved in 80 ml of 20% methanol. The pH of the solution was adjusted to 6.8 to 7.0 by addition of 1N NaOH, whereby compound 1 crystallized. Yield: 55%, mp 220°–235° C.

N-α-(2-Naphthylsulfonyl)-3-cyano-(D,L)-phenylalanine (3)

19.0 g of compound 2 were dissolved in 230 ml of 1N KOH. A solution of 25.0 g of 2-naphthylsulfonylchloride in 200 ml of ether was added and the mixture was stirred for 16 hours at room temperature. The potassium salt of the desired product already began to crystallize out after about 1½ hours. Afterwards, the precipitate was filtered off, washed with ether, dissolved in water by heating and acidified with 3N HCl, whereupon compound 3 crystallized. It was filtered off and recrystallized from acetic acid/water. Yield: 58%, mp 101°–103° C.

N-α-(2-Naphthylsulfonyl)-3-thiocarboxamido-(D,L)-phenylalanine (4)

1.5 g of compound 3 were dissolved in 20 ml of pyridine and 1 5 ml of TEA After introduction of $H_2S$ in the solution for 10 minutes, the reaction mixture was kept for 20 hours at room temperature. The solvent was then evaporated under reduced pressure and the residue was taken up in ethyl acetate and extracted with 1N HCl. The organic phase was washed once with water and dried over $MgSO_4$, whereupon the solvent was evaporated under reduced pressure. Yellow, amorphous product. Yield: 92%.

N-α-(2-Naphthylsulfonyl)-3-S-methyliminothiocarbonyl-(D,L)-phenylalanine-hydroiodide (5)

1.5 g of compound 4 were dissolved in 25 ml of acetone. After addition of 2.5 g of methyl iodide to the solution, the mixture was heated under reflux for 15 minutes in a water bath. After cooling, compound 5 was precipitated by the addition of ether. Yellowish, amorphous powder. Yield: 93%.

N-α-(2-Naphthylsulfonyl)-3-amidino-(D,L)-phenylalanine (6)

1.86 g of compound 5 were dissolved in 25 ml of methanol. After addition of 0.4 g of ammonium acetate to the solution, the mixture was heated for 3 hours at 60° C. in a water bath, whereby compound 6 (betaine) already began to crystallize out. After 24 hours at room temperature, the residue was filtered off, washed with methanol and dried. Yield: 71%, mp 274°–275° C.

For the conversion to the hydrochloride, 0.5 g of betaine was suspended in 5 ml of methanol and 2N ethyl acetate/HCl was added dropwise until a clear solution was obtained and the resulting hydrochloride was precipitated by the addition of ether. Yield: 92%, amorphous product.

N-α-(2-Naphthylsulfonyl)-3-amidino-(D,L)-phenylalanine ester hydrochlorides (7–11, Table 1).

Portions of 0.5 g of the betaine 6 were suspended in 5 ml of the corresponding alcohol, the suspensions were mixed with 0.36 g of p-toluenesulfonic acid and the obtained solutions were heated in a boiling water bath until complete esterification had taken place (checked by TLC). After cooling, the tosylates of the resulting esters were completely precipitated by the addition of ether.

For the conversion to the hydrochlorides, the oily tosylates were dissolved in water and alkalized with 0.5N NaOH, and the released bases were extracted into ethyl acetate. After drying the ethyl acetate phases over $Na_2SO_4$, the solvent was concentrated to about 5 ml by evaporating under reduced pressure. After acidification with 2N ethyl acetate/HCl, compounds 7–11 were precipitated by the addition of ether.

was evaporated under reduced pressure. Compounds 21 and 22 crystallized when triturated with methanol.

Thioimide or imide carboxylate salts, respectively (25–31, Table 4)

Methyl-thioimide carboxylate hydroiodides (25–27, 30, 31, Table 4)

0.7 g of compounds 19–21 as well as 23 and 24 was dissolved in 20 ml of acetone and 5 ml of methanol, the solutions were mixed with a 5-molar quantity of methyl iodide and the reaction mixtures were refluxed for 15 minutes in a water bath. Afterwards, the solvent was evaporated under reduced pressure and the residue triturated with ethanol, whereby compounds 25–27 and 30 crystallized. Compound 31 was precipitated by the addition of ether after the residue was dissolved in a small volume of abs. ethanol.

TABLE 1

N-α-(2-Naphthylsulfonyl)-3-amidino-(D,L)-phenylalanine ester hydrochlorides

| No | SC | $R^1$ | $R^2$ | $R^4$ | n | Y (%) | mp (°C.) |
|---|---|---|---|---|---|---|---|
| 7 | 6 | Amidino | $-OCH_3$ | 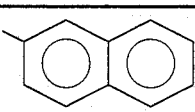 | 0 | 76 | from 137 |
| 8 | 6 | Amidino | $-OCH(CH_3)_2$ | " | 0 | 79 | amorphous |
| 9 | 6 | Amidino | $-n-OC_4H_9$ | " | 0 | 71 | amorphous |
| 10 | 6 | Amidino | $-OCH_2C_6H_5$ | " | 0 | 72 | amorphous |
| 11 | 6 | Amidino | $-OCH_2CH_2C_6H_5$ | " | 0 | 65 | amorphous |

EXAMPLE 2

N-α-(2-Naphthylsulfonyl)-3-amidino-(D,L)-phenylalanine piperidide or piperazide salts, respectively (32–38, Table 5)

N-α-(2-Naphthylsulfonyl)-3-cyano, (D,L)-phenylalanine piperidides or piperazides, respectively (12–18, Table 2)

5.5 mmoles of 2-, 3- and 4-methyl piperidine as well as N-methyl-, N-phenyl-, N-ethoxycarbonyl- and N-t-butoxycarbonyl-piperazine (SC, Table 2) were dissolved in 5 ml of abs. dioxane. After addition of 5 mmoles of NMM, a solution of the acid chloride obtained from compound 3 and thionyl chloride in 10 ml of abs. dioxane was added dropwise and the mixture was stirred for 2 hours at room temperature, whereby compounds 14 and 15 already partially crystallized. Afterwards, the solvent was removed by evaporation under reduced pressure and, after addition of 25 ml of methanol, allowed to crystallize by standing at room temperature. The obtained products were filtered off and purified by recrystallization.

Thioamides (19–24, Table 3)

1.0 g of compounds 12–14 and 16–18 was dissolved in 20 ml of pyridine and 1.5 ml of TEA, $H_2S$ was introduced for 10 minutes into the solutions and the mixtures were left at room temperature for 20 hours. After removal of the solvent by evaporation under reduced pressure, the residue was taken up in ethyl acetate and extracted with 1N HCl. The organic phase was washed once with water and the solvent Methyl-imide carboxylate hydrochlorides (28, 29, Table 4)

1.0 g each of compounds 15 and 16 was suspended in a mixture of 10 ml of abs. dioxane and 10 ml of abs. methanol. 4 g of dried HCl gas were introduced into the suspensions and the obtained solutions were kept in the refrigerator for 5 days, whereby compounds 28 and 29 crystallized. The precipitated products were filtered off, washed with ether and dried in a vacuum desiccator over $KOH/H_2SO_4$.

N-α-(2-Naphthylsulfonyl)-3-amidino-(D,L)-phenylalanine piperidide or piperazide salts, respectively (32–38, Table 5)

Compounds 32–34, 37, 38

0.6 g of the methyl-thioimide carboxylate hydroiodides 25–27 as well as 30 and 31 was diluted or suspended, respectively, in 15 ml of methanol, the reaction mixtures were mixed with a 1.5 molar quantity of ammonium acetate and heated for 3 hours at 60° C. in a water bath. Afterwards, half of the solvent was evaporated off under reduced pressure and the amidine hydroiodides 32–34, 37 and 38 were precipitated by the addition of ether.

Compounds 35 and 36

0.5 g of the methyl-imide carboxylate hydrochlorides 28 and 29 was suspended in 10 ml of abs. ethanol, the suspensions were mixed with ethanolic $NH_3$ solution until the $NH_3$ odor was clearly perceptible and the reaction mixtures were heated for 3 hours at 60° C. in a water bath, whereby clear solutions were obtained already after a short time. After filtration, compounds 35 and 36 were precipitated by the addition of ether.

TABLE 2

N-α-(2-Naphthylsulfonyl)-3-cyano-(D,L)-phenylalanine piperidides or piperazides, respectively

| No SC | R¹ | R² | R⁴ | n | Y (%) | mp (°C.) | Pu |
|---|---|---|---|---|---|---|---|
| 12 | HN⟨⟩—CH₃ (2-methylpiperidine) | —CN | —N⟨⟩—CH₃ (2-methylpiperidine) | 2-naphthyl | 0 | 78 | 192 | CR |
| 13 | HN⟨⟩–CH₂CH₃ (3-methylpiperidine) | —CN | —N⟨⟩–CH₂CH₃ (3-methylpiperidine) | " | 0 | 78 | 190 | CR |
| 14 | HN⟨⟩—CH₃ (4-methylpiperidine) | —CN | —N⟨⟩—CH₃ (4-methylpiperidine) | " | 0 | 81 | 196 | CR |
| 15 | HN⟨⟩N—CH₃ | —CN | —N⟨⟩N—CH₃ | " | 0 | 80 | 181–190 | CR |
| 16 | HN⟨⟩N—C₆H₅ | —CN | —N⟨⟩N—C₆H₅ | " | 0 | 75 | 174–175 | CR |
| 17 | HN⟨⟩N—COOC₂H₅ | —CN | —N⟨⟩N—COOC₂H₅ | " | 0 | 71 | 162–163 | CR |
| 18 | HN⟨⟩N—COOC(CH₃)₃ | —CN | —N⟨⟩N—COOC(CH₃)₃ | " | 0 | 85 | 165–166 | CR |

TABLE 3

Thioamides

| No | SC | R¹ | R² | R⁴ | n | Y (%) | mp (°C.) |
|---|---|---|---|---|---|---|---|
| 19 | 12 | —C(=S)NH₂ | —N⟨⟩—CH₃ (2-methylpiperidine) | 2-naphthyl | 0 | 70 | amorphous |
| 20 | 13 | " | —N⟨⟩–CH₃ (3-methylpiperidine) | " | 0 | 76 | amorphous |

TABLE 3-continued

Thioamides

| No | SC | R¹ | R² | R⁴ | n | Y (%) | mp (°C.) |
|---|---|---|---|---|---|---|---|
| 21 | 14 | " | −N(piperidine)−CH₃ | " | 0 | 90 | 175–176 |
| 22 | 16 | " | −N(piperazine)N−C₆H₅ | " | 0 | 92 | 208–212 |
| 23 | 17 | " | −N(piperazine)N−COOC₂H₅ | " | 0 | 99 | amorphous |
| 24 | 18 | " | −N(piperazine)N−COOC(CH₃)₃ | " | 0 | 94 | amorphous |

TABLE 4

Methyl-thioimide or -imide carboxylate salts, respectively

| No | SC | R¹ | R² | R⁴ | HX | n | Y (%) | mp (°C.) |
|---|---|---|---|---|---|---|---|---|
| 25 | 19 | −C(SCH₃)=NH | −N(piperidine with 2-CH₃) | 2-naphthyl | HI | 0 | 68 | 147–150 |
| 26 | 20 | " | −N(piperidine with 3-CH₃) | " | HI | 0 | 72 | 135–138 |
| 27 | 21 | " | −N(piperidine)−CH₃ | " | HI | 0 | 73 | 202–204 |
| 28 | 15 | −C(OCH₃)=NH | −N(piperazine)N−CH₃ | " | 2 HCl | 0 | 78 | from 168 |
| 29 | 16 | " | −N(piperazine)N−C₆H₅ | " | HCl | 0 | 75 | from 142 |
| 30 | 23 | −C(SCH₃)=NH | −N(piperazine)N−COOC₂H₅ | " | HI | 0 | 89 | 188–192 |
| 31 | 24 | " | −N(piperazine)N−COOC(CH₃)₃ | " | HI | 0 | 81 | amorphous |

TABLE 5

N-α-2-Naphthylsulfonyl)-3-amidino-(D,L)-phenylalanine piperidide or piperazide salts, resp.

| No | SC | R¹ | R² | R⁴ | HX | n | Y (%) | mp (°C.) |
|----|----|----|----|----|----|---|----|----|
| 32 | 25 | Amidino | 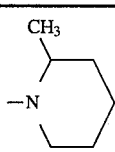 | 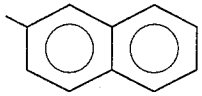 | HI | 0 | 69 | 248–251 |
| 33 | 26 | Amidino | 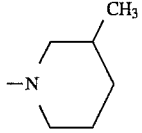 | " | HI | 0 | 70 | 226–228 |
| 34 | 27 | Amidino | 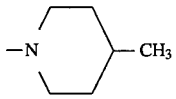 | " | HI | 0 | 77 | 246–248 |
| 35 | 28 | Amidino | 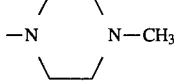 | " | 2 HCl | 0 | 79 | from 130 |
| 36 | 29 | Amidino | 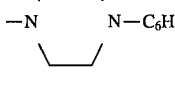 | " | HCl | 0 | 78 | 232–244 |
| 37 | 30 | Amidino | 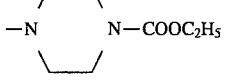 | " | HI | 0 | 67 | 225–227 |
| 38 | 31 | Amidino | 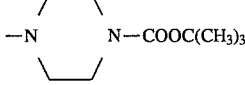 | " | HI | 0 | 69 | 196–198 |

EXAMPLE 3

N-α-2-Naphthylsulfonyl)-3-amidino-(D,L)-phenylalanyl-(D,L)-piperidine carboxylic acids (83–93, Table 10)

N-α-(2-Naphthylsulfonyl)-3-cyano-(D,L)-phenylalanyl-(D,L)-piperidine carboxylates (39–49, Table 6)

The compounds were obtained according to synthetic procedures A and B.

Procedure A: 10 mmoles of the corresponding piperidine carboxylate (SC, Table 6) were dissolved in 10 ml of DMF, mixed with 11 mmoles of HOBT and cooled to 0°. A solution of 9 mmoles of compound 3 in 20 ml of THF and 11 mmoles of DCC were added and the mixture was stirred overnight. The resulting urea derivative was filtered off and the solvent was evaporated under reduced pressure. The residue was dissolved in ethyl acetate, the solution washed with water, 10% citric acid, saturated NaHCO₃ solution and saturated NaCl solution, and finally dried over MgSO₄. After removal of the solvent under reduced pressure, the crude products were purified either by crystallization or column chromatography.

Procedure B: 5.5 mmoles of the corresponding piperidine carboxylate (SC, Table 6) and 5 mmoles of NMM were dissolved in 10 ml of ethyl acetate, a solution of 5 mmoles of the acid chloride obtained from compound 3 and thionyl chloride in 20 ml of ethyl acetate was added dropwise and the reaction mixture stirred for 2 hours at room temperature. The solvent was then evaporated under reduced pressure, the residue was taken up in ethyl acetate, washed with 1N HCl, 10% Na₂CO₃ solution and water. The organic phase was dried over MgSO₄ and the solvent was evaporated under reduced pressure. After addition of 20 ml of methanol, the solution was allowed to crystallize by standing at room temperature. Purification was performed either by crystallization from methanol/water or column chromatography.

N-α-(2-Naphthylsulfonyl)-3-cyano-(D,L)-phenylalanyl-(D,L)-piperidine carboxylic acids (50–60, Table 7)

2 mmoles of compounds 39–49 were either dissolved or suspended in 20 ml of methanol. 10 ml of 1N NaOH were added and the obtained solutions were stirred at room temperature until complete saponification was achieved (checked by TLC). 100 ml of water were then added and the resulting solutions were acidified with 1N HCl. The precipitated products were isolated and, if necessary, purified by either crystallization or column chromatography.

Thioamides (61–71, Table 8)

1.0 g each of compounds 50–60 was dissolved in 20 ml of pyridine and 1.5 ml of TEA, H₂S was introduced in the solutions for 10 minutes and the reaction mixtures were kept at room temperature for 20 hours. The solvent was then evaporated under reduced pressure and the residues were taken up in ethyl acetate and washed with 1N HCl. The organic phase was washed once with water, dried over MgSO₄ and the solvent was evaporated under reduced pressure. Compounds 61–71 were used as obtained without any further purification.

Thioimide carboxylate hydroiodides (72–82, Table 9)

1.0 g each of the thioamides 61–71 was dissolved in 25 ml of acetone, the solutions were mixed with a 15-molar quantity of methyl iodide and the reaction mixtures were kept in the dark at room temperature for 20 hours. Compounds 72–82 were then precipitated by the addition of ether and used in the next step as obtained without any further purification.

N-α-(2-Naphthylsulfonyl)-3-amidino-(D,L)-phenylalanyl-(D,L)-piperidine carboxylic acid hydrochlorides (83–93, Table 10)

0.5 g of the thioimide carboxylate hydroiodides 72–82 was dissolved in 10 ml of methanol, the solutions were mixed with a 1.5-molar quantity of ammonium acetate and the reaction mixtures heated at 60° C. for 3 hours in a water bath. After another 24 hours in the refrigerator, the crystallized betaines 83–93 were filtered off, washed with methanol, ether and dried.

For the conversion into the corresponding hydrochlorides 0.2 g of betaine was suspended in 3 ml of methanol, 2N ethyl acetate/HCl was added dropwise until a clear solution was obtained and the resulting salts were completely precipitated by the addition of ether.

TABLE 64

N-α-(2-Naphthylsulfonyl)-3-cyano-(D,L)-phenylalanyl-(D,L)-piperidine carboxylates

| No SC | R¹ | R² | R⁴ | n | P | Y (%) | mp (°C.) | Pu |
|---|---|---|---|---|---|---|---|---|
| 39 | COOC₂H₅ on piperidine (3-position), HN | —CN, —N piperidine with COOC₂H₅ (3-position) | 2-naphthyl | 0 | A/B | 78 | 138–140 | CR |
| 40 | COOC₂H₅ on piperidine (4-position), HN | —CN, —N piperidine with COOC₂H₅ (4-position) | " | 0 | B | 60 | 182–183 | CR |
| 41 | HN-piperidine-COOC₂H₅ | —CN, —N piperidine-COOC₂H₅ | " | 0 | A/B | 68 | 150–151 | CR |
| 42 | COOCH₃, HN-piperidine-CH₃ | —CN, —N piperidine with COOCH₃ and CH₃ | " | 0 | A | 46 | 170–172 | CR |
| 43 | COOCH₃, HN-piperidine-C₂H₅ | —CN, —N piperidine with COOCH₃ and C₂H₅ | 2-naphthyl | 0 | A | 53 | 158–159 | CR |
| 44 | COOCH₃, HN-piperidine-C(CH₃)₃ | —CN, —N piperidine with COOCH₃ and C(CH₃)₃ | " | 0 | A | 51 | 102–104 | CC |

TABLE 64-continued

N-α-(2-Naphthylsulfonyl)-3-cyano-(D,L)-phenylalanyl-(D,L)-piperidine carboxylates

| No | SC | R¹ | R² | R⁴ | n | P | Y (%) | mp (°C.) | Pu |
|----|----|----|----|----|---|---|-------|----------|----|
| 45 | COOCH₃, CH₃, HN (piperidine) | —CN | COOCH₃, CH₃, —N (piperidine) | " | 0 | A | 34 | 188–190 | CC |
| 46 | COOCH₃, HN, CH₃ (piperidine) | —CN | COOCH₃, —N, CH₃ (piperidine) | " | 0 | B | 45 | 195–197 | CC |
| 47 | COOCH₃, HN—CH₃, CH₃ (piperidine) | —CN | COOCH₃, —N—CH₃, CH₃ (piperidine) | naphthyl | 0 | B | 38 | 152–156 | CR |
| 48 | CH₃, COOC₂H₅, HN (piperidine) | —CN | CH₃, COOC₂H₅, —N (piperidine) | " | 0 | B | 47 | 167–168 | CR |
| 49 | COOCH₃, COOCH₃, HN (piperidine) | —CN | COOCH₃, COOCH₃, —N (piperidine) | " | 0 | A | 42 | amorphous | CC |

TABLE 7

N-α-(2-Naphthylsulfonyl)-3-cyano-(D,L)-phenylalanyl-(D,L)-piperidine carboxylic acids

| No | SC | R¹ | R² | R⁴ | n | Y (%) | mp (°C.) | Pu |
|----|----|----|----|----|---|-------|----------|----|
| 50 | 39 | —CN | COOH, —N (piperidine, 2-position) | naphthyl | 0 | 78 | 177–181 | CC |
| 51 | 40 | —CN | COOH, —N (piperidine, 3-position) | " | 0 | 88 | 204–205 | — |
| 52 | 41 | —CN | —N—COOH (piperidine, 4-position) | " | 0 | 89 | 188–189 | CR |

TABLE 7-continued

N-α-(2-Naphthylsulfonyl)-3-cyano-(D,L)-phenylalanyl-(D,L)-piperidine carboxylic acids

| No | SC | R¹ | R² | R⁴ | n | Y (%) | mp (°C.) | Pu |
|---|---|---|---|---|---|---|---|---|
| 53 | 42 | —CN | COOH, —N piperidine with 4-CH₃ | " | 0 | 79 | amorphous | — |
| 54 | 43 | —CN | COOH, —N piperidine with 4-C₂H₅ | naphthyl | 0 | 69 | from 165 | CC |
| 55 | 44 | —CN | COOH, —N piperidine with 4-C(CH₃)₃ | " | 0 | 73 | from 110 | CC |
| 56 | 45 | —CN | COOH, CH₃, —N piperidine | " | 0 | 91 | amorphous | — |
| 57 | 46 | —CN | COOH, —N piperidine with CH₃ | " | 0 | 90 | 181–185 | — |
| 58 | 47 | —CN | COOH, —N piperidine with CH₃, CH₃ | naphthyl | 0 | 93 | amorphous | — |
| 59 | 48 | —CN | CH₃, COOH, —N piperidine | " | 0 | 91 | 97–103 | — |
| 60 | 49 | —CN | COOH, COOH, —N piperidine | " | 0 | 77 | 118–123 | CC |

TABLE 8

Thioamides

| No | SC | R¹ | R², R⁴, n | Y (%) | mp (°C.) |
|---|---|---|---|---|---|
| 61 | 50 | —C(=S)NH₂ | like 50 | 96 | amorphous |
| 62 | 51 | " | like 51 | 93 | amorphous |
| 63 | 52 | " | like 52 | 87 | from 126 |
| 64 | 53 | " | like 53 | 95 | amorphous |
| 65 | 54 | " | like 54 | 96 | amorphous |

TABLE 8-continued

Thioamides

| No | SC | R¹ | R², R⁴, n | Y (%) | mp (°C.) |
|---|---|---|---|---|---|
| 66 | 55 | " | like 55 | 94 | amorphous |
| 67 | 56 | " | like 56 | 98 | amorphous |
| 68 | 57 | " | like 57 | 94 | amorphous |
| 69 | 58 | " | like 58 | 90 | amorphous |
| 70 | 59 | " | like 59 | 97 | amorphous |
| 71 | 60 | " | like 60 | 94 | amorphous |

TABLE 9

Thioimide carboxylate hydroiodides

| No | SC | R¹ | R², R⁴, n | Y (%) | mp (°C.) |
|---|---|---|---|---|---|
| 72 | 61 | −C(SCH₃)=NH | like 50 | 52 | 192–194 (dec) |
| 73 | 62 | " | like 51 | 67 | from 140 (dec) |
| 74 | 63 | " | like 52 | 65 | from 185 (dec) |
| 75 | 64 | " | like 53 | 85 | amorphous |
| 76 | 65 | " | like 54 | 73 | amorphous |
| 77 | 66 | " | like 55 | 61 | amorphous |
| 78 | 67 | " | like 56 | 79 | amorphous |
| 79 | 68 | " | like 57 | 90 | amorphous |
| 80 | 69 | " | like 58 | 58 | 158–162 (dec) |
| 81 | 70 | " | like 59 | 94 | from 130 (dec) |
| 82 | 71 | " | like 60 | 88 | amorphous |

TABLE 10

N-α-(2-Naphthylsulfonyl)-3-amidino-(D,L)-phenylalanyl-(D,L)-piperidine carboxylic acid hydrochlorides

| No | SC | R¹ | R², R⁴, n | Y (%) | mp (°C.) Betaine | mp (°C.) Hydrochloride |
|---|---|---|---|---|---|---|
| 83 | 72 | Amidino | like 50 | 92 | 208–212 | from 155 |
| 84 | 73 | Amidino | like 51 | 80 | 242–245 | from 148 |
| 85 | 74 | Amidino | like 52 | 86 | 247–248 | from 155 |
| 86 | 75 | Amidino | like 53 | 64 | 208–212 | from 145 |
| 87 | 76 | Amidino | like 54 | 53 | 225–227 | from 140 |
| 88 | 77 | Amidino | like 55 | 50 | 226–228 | from 155 |
| 89 | 78 | Amidino | like 56 | 86 | 214–218 | from 150 |
| 90 | 79 | Amidino | like 57 | 68 | 225–228 | from 153 |
| 91 | 80 | Amidino | like 58 | 66 | 204–210 | from 158 |
| 92 | 81 | Amidino | like 59 | 76 | from 245 | from 145 |
| 93 | 82 | Amidino | like 60 | 30 | 275–278 | from 110 |

EXAMPLE 4

N-α-(2-Naphthylsulfonyl)-3-amidino-(D,L)-phenylalanyl-methyl-(D,L)-piperidine carboxylate hydrochlorides (94–101, Table 11)

0.2 g of the betaines 83–87, 89, 90 and 92 was suspended in 5 ml of abs. methanol, the suspensions were mixed with 1–2 ml of 2M ethyl acetate/HCl and the thereby obtained solutions were left standing at room temperature until complete esterification (checked by TLC) was achieved. The hydrochlorides 94–101 (Table 11) were precipitated by the addition of ether.

TABLE 11

N-α-(2-Naphthylsulfonyl)-(D,L)-3-amidino-phenylalanyl-methyl-(D,L)-piperidine carboxylate hydrochlorides

| No | SC | R¹ | R² | R⁴ | n | Y (%) | mp (°C.) |
|---|---|---|---|---|---|---|---|
| 94 | 83 | Amidino | 2-COOCH₃-piperidinyl | 2-naphthyl | 0 | 62 | from 135 |
| 95 | 84 | Amidino | 3-COOCH₃-piperidinyl | " | 0 | 73 | from 130 |
| 96 | 85 | Amidino | 4-COOCH₃-piperidinyl | " | 0 | 76 | from 140 |
| 97 | 86 | Amidino | 2-COOCH₃-6-CH₃-piperidinyl | " | 0 | 88 | from 125 |

TABLE 11-continued

N-α-(2-Naphthylsulfonyl)-(D,L)-3-amidino-phenylalanyl-methyl-(D,L)-piperidine carboxylate hydrochlorides

| No | SC | R¹ | R² | R⁴ | n | Y (%) | mp (°C.) |
|----|----|----|----|----|----|-------|----------|
| 98 | 87 | Amidino | COOCH₃, –N(piperidine)–C₂H₅ | naphthyl | 0 | 92 | amorphous |
| 99 | 89 | Amidino | COOCH₃, CH₃, –N(piperidine) | " | 0 | 83 | from 130 |
| 100 | 90 | Amidino | COOCH₃, –N(piperidine), CH₃ | " | 0 | 84 | amorphous |
| 101 | 92 | Amidino | CH₃, COOCH₃, –N(piperidine) | " | 0 | 97 | from 150 |

EXAMPLE 5

N-α-(2-Naphthylsulfonyl)-3-amidino-(D,L)-phenylalanyl-isonipecotyl-4-aminobutyric acid and -6-aminocaproic acid (110, 111, Table 12)

N-α-(2-Naphthylsulfonyl)-3-cyano-(D,L)-phenylalanyl-isonipecotyl-ethyl-4-aminobutyrate and -methyl-6-aminocaproate (102, 103, Table 12)

9 mmoles of compound 52 (example 3) were reacted with 10 mmoles each of ethyl-4-aminobutyrate and methyl-6-aminocaproate, respectively, as described in procedure A (example 3). Purification was performed by column chromatography over silica gel 60 with chloroform (for 102) and chloroform/methanol 98:2 (for 103) as eluent.

N-α-(2-Naphthylsulfonyl)-3-cyano-(D,L)-phenylalanyl-isonipecotyl-4-aminobutyric acid and -6-aminocaproic acid (104, 105, Table 12)

2 mmoles of compounds 102 and 103 were saponified as described in example 3 (50–60). Compound 104 was crystallized from ethyl acetate. The purification of 105 was performed by column chromatography over silica gel 60 with chloroform/methanol 95:5 as eluent.

Thioamides (106, 107, Table 12)

1.0 g each of compounds 104 and 105 was converted and worked up as described in example 3 (61–71).

Methyl-thioimide carboxylate hydroiodides (108, 109; Table 12)

0.7 g of compounds 106 and 107 was dissolved each in 20 ml of acetone, the solutions were mixed with a 5-molar quantity of methyl iodide and the reaction mixtures were heated under reflux for 15 minutes in a water bath. The solvent was then evaporated under reduced pressure, the residues were suspended in 2 ml of abs. ethanol and left to crystallize at room temperature. The crystalline products 108 and 109 were filtered off, washed with ether and dried.

N-α-(2-Naphtylsulfonyl)-3-amidino-(D,L)-phenylalanyl-isonipecotyl-4-aminobutyric acid and -6-aminocaproic acid hydroiodide (110, 111; Table 12)

0.5 g of the methyl-thioimide carboxylate hydroiodides 108 and 109 was dissolved each in 10 ml of methanol, the solutions were mixed with a 1.5-molar quantity of ammonium acetate and the reaction mixtures were heated for 3 hours at 60° C. in a water bath. After cooling, compounds 110 and 111 were precipitated by the addition of ether. Purification was performed by precipitating from ethanol/ether.

TABLE 12

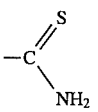

| No | SC | R¹ | R² | Y (%) | mp (°C.) |
|---|---|---|---|---|---|
| 102 | 52 | —CN | —NH(CH₂)₃—COOC₂H₅ | 62 | 110–112 |
| 103 | 52 | —CN | —NH(CH₂)₅—COOCH₃ | 60 | 130–135 |
| 104 | 102 | —CN | —NH(CH₂)₃—COOH | 91 | 183–185 |
| 105 | 103 | —CN | —NH(CH₂)₅—COOH | 63 | amorphous |
| 106 | 104 | —C(=S)NH₂ | —NH(CH₂)₃—COOH | 97 | amorphous |
| 107 | 105 | " | —NH(CH₂)₅—COOH | 93 | amorphous |
| 108 | 106 | —C(SCH₃)=NH .HI | —NH(CH₂)₃—COOH | 85 | 174–178 |
| 109 | 107 | " | —NH(CH₂)₅—COOH | 66 | 160–162 |
| 110 | 108 | —C(NH)NH₂ .HI | —NH(CH₂)₃—COOH | 79 | from 152 |
| 111 | 109 | " | —NH(CH₂)₅—COOH | 81 | from 110 |

EXAMPLE 6

N-α-(2-Naphthylsulfonyl)-3-amidino-(D,L)-phenylalanyl-(D,L)-pipecolyl-glycine and -methyl ester (116, 117)

N-α-(2-Naphthylsulfonyl)-3-cyano-(D,L)-phenylalanyl-(D,L)-pipecolyl-glycine-t-butyl ester (112)

9 mmoles of compound 50 and 10 mmoles of glycine-t-butyl ester were coupled and worked up according to procedure A (example 3). The purification of compound 112 was performed by column chromatography over silica gel 60 with chloroform as the eluent. Yield: 70%, mp 121°–125° C.

N-α-(2-Naphthylsulfonyl)-3-thiocarboxamido-(D,L)-phenylalanyl-(D,L)-pipecolyl-glycine-t-butyl ester (113)

1.3 g of compound 112 was converted as described in example 3 (61–71). Amorphous product. Yield: 95%.

N-α-(2-Naphthylsulfonyl)-3-S-methyliminothiocarbonyl-(D,L)-phenylalanyl-(D,L)-pipecolyl-glycine-t-butyl ester hydroiodide (114)

1.3 g of compound 113 was dissolved in 35 ml of acetone, the solution was mixed with 4.3 g of methyl iodide and the preparation was kept in the dark at room temperature for 20 hours. Compound 104 was then precipitated by the addition of ether. Amorphous product. Yield: 76%.

N-α-(2-Naphthylsulfonyl)-3-amidino-(D,L)-phenylalanyl-(D,L)-pipecolyl-glycine-t-butyl ester hydroiodide (115)

1.2 g of compound 114 was converted and worked up as described in example 2 (32–34). Yield: 96%, mp from 90° C.

N-α-(2-Naphthylsulfonyl)-3-amidino-(D,L)-phenylalanyl-(D,L)-pipecolyl-glycine hydrochloride (116)

0.95 g of compound 115 was converted to its free base by suspending the substance in 250 ml of ethyl acetate and washing it with 30 ml of 0.2N NaOH. The organic phase was washed with water, dried over MgSO₄ and the solvent was evaporated under reduced pressure. The residue (0.77 g) was dissolved in 6 ml of TFA, the solution was stirred for 2 hours at room temperature and the solvent was then removed by evaporation under reduced pressure. The residue was dissolved in 8 ml of methanol, the solution was mixed with 2 ml of 2N ethyl acetate/HCl and compound 116 was precipitated with ether. Yield: 68%, mp from 155° C.

N-α-(2-Naphthylsulfonyl-3-amidino-(D,L)-phenylalanyl-(D,L)-pipecolyl-glycine-methyl ester hydrochloride (117)

0.2 g of compound 116 was converted as described in example 4. Yield: 86%, mp from 145° C.

EXAMPLE 7

N-α-(2-Naphthylsulfonyl)-3-amidino-(L)-phenylalanyl-(D)-proline and -methyl ester (123, 124)

N-α-(2-Naphthylsulfonyl)-3-cyano-(D)-phenylalanyl-(D)-proline-t-butyl ester and N-α-(2-Naphthylsulfonyl)-3-cyano-(L)-phenylalanyl-(D)-proline-t-butyl ester (118, 119)

11 mmoles of compound 3 and 12 mmoles of (D)-proline-t-butyl ester were coupled according to procedure A (example 3). 4.9 g of a mixture of compounds 118 and 119 were obtained. Column chromatography over silica gel 60 with chloroform as the eluent yielded:
on the one hand N-α-(2-naphthylsulfonyl)-3-cyano-(D)-phenylalanyl-(D)-proline-t-butyl ester (118). Yield: 28%, amorphous, $[\alpha]_D^{20}+39°$ (1% in methanol), and on the other hand colorless crystals of N-α-(2-naphthylsulfonyl)-3-cyano-(L)-phenylalanyl-(D)-proline-t-butyl ester (119). Yield: 33%, mp 139°–141° C.; $[\alpha]_D^{20}+35°$ (1% in methanol).

N-α-(2-Naphthylsulfonyl)-3-thiocarboxamido-(L)-phenylalanyl-(D)-proline-t-butyl ester (120)

1.0 g of compound 119 was converted and worked up as described in example 3 (61–71). Amorphous product. Yield: 92%.

N-α-(2-Naphthylsulfonyl)-3-S-methyliminothiocarbonyl-(L)-phenylalanyl-(D)-proline-t-butyl ester hydroiodide (121)

0.95 g of compound 120 was reacted in 30 ml of acetone and worked up as described in example 2 (25–31), whereby a crystalline product was obtained. Yield: 92%, mp from 160° C.

N-α-(2-Naphthylsulfonyl)-3-amidino-(L)-phenylalanyl-(D)-proline-t-butyl ester hydroiodide (122)

1.0 g of methyl-thioimide carboxylate hydroiodide (121) was converted in 10 ml of methanol and worked up as described in example 2 (32–34). Yield: 96%, mp from 130° C.

N-α-(2-Naphthylsulfonyl)-3-amidino-(L)-phenylalanyl-(D)-proline hydrochloride (123)

0.75 g Of compound 122 was dissolved in a mixture of 5 ml of TFA and 5 ml of isopropanol. Completion of ester hydrolysis was checked by HPLC. The solvent was then evaporated under reduced pressure. The oily residue was dissolved in 10 ml of methanol and ethanolic ammonia solution was added to the solution until a pH value of 7.4 was reached. The precipitated betaine was filtered off after 2 hours and dried. Yield: 56%, mp 215°–223° C.

For the conversion into the hydrochloride, the obtained betaine was dissolved in methanolic hydrochloric acid and ether was added. The precipitated hydrochloride was filtered off, washed with ether and dried. Yield: 85%, mp from 145° C.

N-α-(2-Naphthylsulfonyl)-3-amidino-(L)-phenylalanyl-(D)-proline-methyl ester hydrochloride (124)

0.22 g of betaine 123 was converted and worked up as described in example 4. Yield: 74%, mp from 150° C.

Moreover, to prove that the structure and the designated rotations indeed were correct, a stereospecific synthesis was carried out by enzymatically hydrolysing 3-cyano-(D,L)-phenylalanine methyl ester with chymotrypsin giving the optically pure isomer 3-cyano-(L)-phenylalanine (125) which was converted into Nα-(2-naphthylsulfonyl)-3-cyano-(L)-phenylalanine (126) with 2-naphthylsulfonyl chloride. The coupling of compound 126 with (D)-proline-t-butyl ester according to the DCC method led to Nα-(2-naphthylsulfonyl)-3-cyano-(L)-phenylalanyl-(D)-proline-t-butyl ester (127), from which Nα-(2-naphthylsulfonyl)-3-amidino-(L)-phenylalanyl-(D)-proline was synthesized according to the procedure described for compounds 120–123. The intermediate products obtained as well as the end product were identical to compounds 120–123 as shown by TLC. The determined melting points, rotational values and $K_i$ values also corresponded.

3-Cyano-(L)-phenylalanine hydrochloride (125)

4.8 g of the 3-cyano-(D,L)-phenylalanine methyl ester obtained from compound 2 by esterification with methanol in the presence of p-toluenesulfonic acid were dissolved in 25 ml of toluene, a solution of 0.2 g of chymotrypsin in 25 ml of water was added and the mixture was stirred for 1 hour at room temperature, the formed precipitate was filtered off, washed with water and dried. The dried product was suspended in 10 ml of methanol and acidified with 2N ethyl acetate/HCl. After filtration, 0.55 g of compound 125 was obtained by the addition of a large volume of ether to the filtrate. The remaining filtrate reaction solvent (toluene/water) was extracted 3 times with ethyl acetate. After separation of the phases, the aqueous phase was dried by removing the water under reduced pressure and the resulting residue was treated as described above. 1.8 g of compound 125 was additionally obtained. Total yield: 88%, mp 211°–212° C. $[\alpha]_D^{20}-10.3°$ (3% in methanol).

From the ethyl acetate extracts of the reaction solvent toluene/water, 3-cyano-(D)-phenylalanine methyl ester was obtained in an oily form, the acid hydrolysis of which (25 ml 0.5N HCl, 6 hours reflux) led to 3-cyano-(D)-phenylalanine hydrochloride. Yield: 72%, mp 210°–212° C., $[\alpha]_D^{20}+10.0°$ (3% in methanol).

N-α-(2-Naphthylsulfonyl)-3-cyano-(L)-phenylalanine (126)

2.2 g of compound 125 were dissolved in a mixture of 10.4 ml of 1N KOH and 1.0 g of NaHCO$_3$ in 12 ml of water, a solution of 2.64 g of 2-naphthylsulfonyl chloride in 30 ml of ether was added and the mixture was stirred for 16 hours at room temperature. The precipitated potassium salt of compound 126 was filtered off and washed with ether. For the conversion into the free acid, the potassium salt was suspended in 50 ml of water, the suspension was acidified with 1N HCl and extracted with ethyl acetate. The organic phase was washed once with water, dried over MgSO$_4$ and the solvent was removed by evaporation under reduced pressure. Amorphous product. Yield: 62%. $[\alpha]_D^{20}+8.2°$ (5% in methanol).

N-α-(2-Naphthylsulfonyl)-3-cyano-(L)-phenylalanyl-(D)-proline-t-butyl ester (127)

0.5 g of compound 126 was coupled to (D)-proline-t-butyl ester and worked up as described for compounds 118 and 119 (procedure A, example 3). After column chromatography over silica gel 60 with chloroform as the eluent, colorless crystals of compound 127 were obtained. Yield: 80%, mp 139°–141° C., $[\alpha]_D^{20}+35°$ (1% in methanol).

EXAMPLE 8

N-α-(2-Naphtylsulfonyl)-3-amidino-(D,L)-phenylalanyl-1,2,3,4-tetrahydroisoquinoline-3-carbonic acid and -methyl ester (134, 135)

N-α-(2-Naphthylsulfonyl)-3-cyano-(D,L)-phenylalanyl-1,2,3,4-tetrahydroisoquinoline-3-carbonic acid methyl ester (128, Table 13)

11 mmoles of 1,2,3,4-tetrahydroisoquinoline-3-carboxylic acid methyl ester and 10 mmoles of the acid chloride obtained from compound 3 and thionyl chloride were coupled and worked up according to procedure B (example 3). Purification was performed by crystallization from methanol.

N-α-(2-Naphthylsulfonyl)-3-cyano-(D,L)-phenylalanyl-1,2,3,4-tetrahydroisoquinoline-3-carboxylic acid (129, Table 13)

2 mmoles of compound 128 were saponified as described in example 3 (50–60). Compound 129 was used as obtained in the next step.

Thioamides (130, 131, Table 13)

1.0 g each of compounds 128 and 129 was converted and worked up as described in example 3 (61–71).
Methyl-thioimide carboxylate hydroiodides (132, 133, Table 13)
1.0 g each of compounds 130 and 131 was converted and worked up as described in example 3 (72–82).

N-α-(2-Naphtylsulfonyl)-3-amidino-(D,L)-phenylalanyl-1,2,3,4-tetrahydroisoquinoline-3-carboxylic acid and -methyl ester hydroiodides (134, 135, Table 13)

0.5 g each of the methyl-thioimide carboxylate hydroiodides 132 and 133 was converted and worked up as described in example 2 (32–34).

TABLE 13

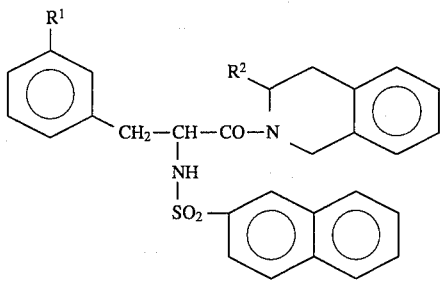

| No | SC | R¹ | R² | Y (%) | mp (°C.) |
|---|---|---|---|---|---|
| 128 | 3 | —CN | —COOCH₃ | 75 | 182–183 |
| 129 | 128 | —CN | —COOH | 92 | 218–220 |
| 130 | 129 | —C(=S)NH₂ | —COOH | 94 | amorphous |
| 131 | 128 | —C(=S)NH₂ | —COOCH₃ | 88 | amorphous |
| 132 | 130 | —C(SCH₃)=NH ·HI | —COOH | 86 | amorphous |
| 133 | 131 | —C(SCH₃)=NH ·HI | —COOCH₃ | 70 | amorphous |
| 134 | 132 | —C(NH₂)=NH ·HI | —COOH | 73 | from 168 |
| 135 | 133 | —C(NH₂)=NH ·HI | —COOCH₃ | 76 | from 133 |

EXAMPLE 9

N-α-(2-Naphthylsulfonyl)-3-amidino-(D,L)-phenylalanyl-sarcosine and -methyl ester (140, 141)

N-α-(2-Naphthylsulfonyl)-3-cyano-(D,L)-phenylalanyl-sarconsine-t-butyl ester (136)

9 mmoles of compound 3 and 10 mmoles of sarcosine-t-butyl ester were converted and worked up according to procedure A (example 3). Purification was performed by column chromatography over silica gel 60 with chloroform as the eluent. Yield: 82%, mp 141°–142° C.

N-α-(2-Naphthylsulfonyl)-3-thiocarboxamido-(D,L)-phenylalanyl-sarcosine-t-butyl ester (137)

2.0 g of compound 136 were converted and worked up as described in example 3 (61–71). Yield: 89%, mp 162°–164° C.

N-α-(2-Naphthylsulfonyl)-3-S-methyliminothiocarbonyl-(D,L)-phenylalanyl-sarcosine-t-butyl ester (138)

1.8 g of compound 137 was converted and worked up in 40 ml of acetone as described in example 3 (72–82). Yield: 92%, mp from 105° C.

N-α-(2-Naphthylsulfonyl)-3-amidino-(D,L)-phenylalanyl-sarcosine-t-butyl ester hydroiodide (139)

2.0 g of compound 138 were converted and worked up in 20 ml of methanol as described in example 2 (32–34). Yield: 74%, mp from 103° C.

N-α-(2-Naphthylsulfonyl)-3-amidino-(D,L)-phenylalanyl-sarcosine hydrochloride (140)

0.57 g of the base of compound 139, obtained as described in example 6 (116), was dissolved in 7 ml of TFA, the solution was stirred for 3 hours at room temperature and the solvent was evaporated under reduced pressure. The residue was dissolved in 5 ml of methanol, the solution was mixed with 2 ml of 2N ethyl acetate/HCl and compound 140 was precipitated by the addition of ether. Yield: 70%, mp from 130° C.

N-α-(2-Naphthylsulfonyl)-3-amidino-(D,L)-phenylalanyl-sarcosine-methyl ester hydrochloride (141)

0.2 g of compound 140 was converted as described in example 4. Yield: 75%, mp 125°–135° C.

EXAMPLE 10

N-α-(2-Naphthylsulfonyl)-3-amidino-(D,L)-phenylalanyl-decahydroquinoline-4-carboxylic acid (146)

N-α-(2-Naphthylsulfonyl)-3-cyano-(D,L)-phenylalanyl-decahydroquinoline-4-carboxylic acid methyl ester (142)

5.5 mmoles of decahydroquinoline-4-carboxylic acid methyl ester and 5 mmoles of the acid chloride obtained from compound 3 and thionyl chloride were converted and worked up according to procedure B (example 3). Purification was performed by column chromatography over silica gel 60 with chloroform as the eluent. Yield: 28%, mp 193°–195° C.

N-α-(2-Naphthylsulfonyl)-3-cyano-(D,L)-phenylalanyl-decahydroquinoline-4-carboxylic acid (143)

1.0 g of compound 142 was saponified as described in example 3 (50–60). Purification was performed by column chromatography over silica gel 60 with chloroform as the eluent. Yield: 83%, mp 263°–266° C.

N-α-(2-Naphthylsulfonyl)-3-thiocarboxamido-(D,L)-phenylalanyl-decahydroquinoline-4-carboxylic acid (144)

0.95 g of compound 143 was converted and worked up as described in example 3 (61–71). Amorphous product. Yield: 87%.

N-α-(2-Naphthylsulfonyl)-3-S-methyliminothiocarbonyl-(D,L)-phenylalanyl-decahydroquinoline-4-carboxylic acid hydroiodide (145)

0.87 g of compound 144 was dissolved in 20 ml of acetone, the solution was mixed with 3 g of methyl iodide and the reaction mixture was left at room temperature for 20 hours, whereby compound 145 crystallized. The crystals were filtered off, washed with acetone/ether 1:1 and dried. Yield: 65%, mp 153°–157° C.

N-α-(2-Naphthylsulfonyl)-3-amidino-(D,L)-phenylalanyl-decahydroquinoline-4-carboxylic acid hydroiodide (146)

0.68 g of compound 145 was converted as described in example 3 (83–93), whereby the amidine hydroiodide 146 crystallized. Yield: 54%, mp 188°–192° C.

EXAMPLE 11

N-α-(2-Naphthylsulfonyl)-3-amidino-(D,L)-phenylalanyl-decahydroisoquinoline-3-carboxylic acid (151)

N-α-(2-Naphthylsulfonyl)-3-cyano-(D,L)-phenylalanyl-decahydroisoquinoline-3-carboxylic acid methyl ester (147)

10 mmoles of decahydroisoquinoline-3-carboxylic acid methyl ester and 9 mmoles of compound 3 were coupled and worked up according to procedure A (example 3). Purification was performed by column chromatography over silica gel 60 with chloroform as the eluent. Amorphous product. Yield: 29%.

N-α-(2-Naphthylsulfonyl)-3-cyano-(D,L)-phenylalanyl-decahydroisoquinoline-3-carboxylic acid (148)

0.77 g of compound 147 was saponified as described in example 3 (50–60). Purification was performed by column chromatography over silica gel 60 with chloroform/methanol 90:10 as eluent. Yield: 83%, mp from 145° C.

N-α-(2-Naphthylsulfonyl)-3-thiocarboxamido-(D,L)-phenylalanyl-decahydroisoquinoline-3-carboxylic acid (149)

0.52 g of compound 148 was converted and worked up as described in example 2 (19–24). Amorphous product. Yield: 91%.

N-α-(2-Naphthylsulfonyl)-3-S-methyliminothiocarbonyl-(D,L)-phenylalanyl-decahydroisoquinoline-3-carboxylic acid (150)

0.5 g of compound 149 was dissolved in 20 ml of acetone, the solution was mixed with 2.0 g of methyl iodide and the reaction mixture was kept in the dark at room temperature for 20 hours, whereafter compound 150 was precipitated by the addition of ether. Amorphous product. Yield: 69%.

N-α-(2-Naphthylsulfonyl)-3-amidino-(D,L)-
phenylalanyl-decahydroisoquinoline-3-carboxylic
acid hydrochloride (151).

0.4 g of methyl-thioimide carboxylate hydroiodide 150 was converted as described in example 3 (83–93), whereby the corresponding betaine was obtained. Yield: 64%, mp 214°–218° C.

The hydrochloride was obtained as described in example 3 (83–93). Yield: 92%, mp from 168° C.

EXAMPLE 12

N-α-(2-Naphthylsulfonyl)-glycyl-3-amidino-(D,L)-
phenylalanine-4-methylpiperidide (156 )

N-α-2-Naphthylsulfonyl)-glycyl-3-cyano-(D,L)-
phenylalanine (152)

20 mmoles of compound 3 were dissolved in 42 ml of 1N NaOH, a solution of 22 mmoles of 2-naphthylsulfonyl-glycyl chloride in 60 ml of ethyl acetate was added and the reaction mixture was stirred for 16 hours. Afterwards, a small amount of insoluble by-product was filtered off, the phases separated and the aqueous phase acidified with 1N HCl and extracted with ethyl acetate. The organic phase was washed once with water, dried over $MgSO_4$ and the solvent was evaporated under reduced pressure. The amorphous residue crystallized by triturating with ether. The product crystallized from dilute acetic acid. Yield: 72%, mp 157°–158° C.

N-α-(2-Naphthylsulfonyl)-glycyl-3-cyano-(D,L)-
phenylalanine-4-methylpiperidide (153)

10 mmoles of compound 152 and 12 mmoles of 4-methylpiperidine were converted and worked up according to procedure A (example 3). Purification was achieved by column chromatography over silica gel 60 with chloroform/methanol 90:10 as eluent. Yield: 94%, mp 170°–172° C.

N-α-(2-Naphthylsulfonyl)-glycyl-3-thiocarboxamido-
(D,L)-phenylalanine- 4-methylpiperidide
(154)

2.6 g of compound 153 were converted in 25 ml of pyridine and 1.5 ml of TEA as described in example 2 (19–24). After distillation of the solvent under reduced pressure, the solid residue was triturated with 60 ml of methanol and 10 ml of 1N HCl, filtered off, washed with methanol and dried. Yield: 96%, mp 190°–192° C.

N-α-(2-Naphthylsulfonyl)-glycyl-3-S-
methyliminothiocarbonyl-(D,L)-phenylalanine-
4-methylpiperidide-hydroiodide (155)

1.0 g of compound 154 was dissolved by heating in 2 ml of DMF. 40 ml of acetone and 3.5 g of methyl iodide were added and the solution was stirred for 4 hours at room temperature, whereby compound 155 crystallized. The residue was then filtered off, washed with ether and dried. Yield: 83%, mp 185°–188° C. (dec).

N-α-(2-Naphthylsulfonyl)-glycyl-3-amidio-(D,L)-
phenylalanine-4-methylpiperidide-hydroiodide (156)

0.8 g of the methyl-thioimide carboxylate hydroiodide 155 was dissolved in a mixture of 18 ml of DMF and 9 ml of methanol, 0.2 g of ammonium acetate was added to the solution and the reaction mixture was heated at 60° C. for 3 hours in a water bath. The solvent was then evaporated under reduced pressure, the residue was dissolved in ethanol and compound 156 was precipitated by the addition of ether. Yield: 78%, mp from 125° C.

EXAMPLE 13

N-α-(2-Naphthylsulfonyl)-glycyl-3-amidino-
(D,L)-phenylalanyl-piperidine carboxylic acids
(165, 166, Table 14)

N-α-(2-Naphthysulfonyl)-glycyl-3-cyano-
(D,L)-phenylalanyl-ethyl-piperidine carboxylates
(157, 158, Table 14)

10 mmoles each of compound 152 and 15 mmoles of the corresponding ethyl-piperidine carboxylate were converted and worked up according to procedure A (example 3). Purification was performed by column chromatography over silica gel 60 with chloroform as the eluent.

N-α-(2-Naphthylsulfonyl)-glycyl-3-cyano
-(D,L)-phenylalanyl-piperidine carboxylic acids
(159, 160, Table 14)

4 mmoles each of compounds 157 and 158 were saponified as described in example 3 (50–60). Purification was achieved by column chromatography over silica gel 60 with chloroform/methanol 90:10 as eluent.

Thioamides (161, 162, Table 14)

0.8 g each of compounds 159 and 160 was converted into the thioamides 161 and 162 as described in example 2 (19–24).

Methyl-thioimide carboxylate hydroiodides (163, 164, Table 14)

0.7 g each of the thioamides 161 and 162 was converted into the compounds 163 and 164 as described in example 3 (72–82).

N-α-(2-Naphthylsulfonyl)-glycyl-3-amidino-(D,L)-
phenylalanyl-piperidine carboxylic acid
hydroiodides (165, 166, Table 14)

0.6 g each of the methyl-thioimide carboxylate hydroiodides 163 and 164 was converted into the amidine hydroiodides 165 and 166 as described in example 2 (32–34).

TABLE 14

[Structure: R¹-phenyl-CH₂-CH(NH-CO-CH₂-NH-SO₂-naphthyl)-CO-N-piperidine-R²]

| No | SC | R¹ | R² | Position R² | Y (%) | mp (°C.) |
|---|---|---|---|---|---|---|
| 157 | 152 | —CN | —COOC₂H₅ | 2 | 72 | amorphous |
| 158 | 152 | —CN | —COOC₂H₅ | 4 | 74 | 146–147 |
| 159 | 157 | —CN | —COOH | 2 | 53 | from 103 |
| 160 | 158 | —CN | —COOH | 4 | 60 | 194–198 |
| 161 | 159 | —C(=S)NH₂ | —COOH | 2 | 94 | amorphous |
| 162 | 160 | " | —COOH | 4 | 85 | amorphous |
| 163 | 161 | —C(SCH₃)=NH ·HI | —COOH | 2 | 58 | amorphous |
| 164 | 162 | " | —COOH | 4 | 68 | amorphous |
| 165 | 163 | —C(NH)NH₂ ·HI | —COOH | 2 | 83 | from 123 |
| 166 | 164 | " | —COOH | 4 | 74 | from 112 |

EXAMPLE 14

N-α-(8-quinolinesulfonyl)-3-amidino-(D,L)-phenylalanine-4-methylpiperidide (171)

N-α-(8-quinolinesulfonyl)-3-cyano-(D,L)-phenylalanine (167)

10 mmoles of compound 3 were dissolved in 22 ml of 1N KOH, a solution of 11 mmoles of 8-quinolinesulfonyl chloride in a mixture of 27 ml of ether/DMF 2:1 was added and the reaction mixture was stirred for 16 hours. The aqueous phase was then separated, acidified with a 10% citric acid solution and extracted with ethyl acetate. The organic phase was washed once with water, dried over MgSO₄ and the solvent was evaporated under reduced pressure. The residue was crystallized from ethyl acetate. Yield: 53%, mp 187°–189° C.

N-α-(8-quinolinesulfonyl)-3-cyano-(D,L)-phenylalanine-4-methylpiperidide (168)

5 mmoles of compound 167 and 7.5 mmoles of 4-methylpiperidine were converted and worked up according to procedure A (example 3). Purification was achieved by column chromatography over silica gel 60 with chloroform as the eluent. Amorphous product. Yield: 61%.

N-α-(8-quinolinesulfonyl)-3-thiocarboxamido-(D,L)-phenylalanine- 4-methylpiperidide (169)

1.4 g of compound 168 was converted as described in example 3 (61–71). Instead of 1N HCl, a 10% citric acid solution was used during work up. Amorphous product. Yield: 62%.

N-α-(8-quinolinesulfonyl)-3-S-methyliminothiocarbonyl-(D,L)-phenylalanine-4-methylpiperidide (170)

0.9 g of the thioamide 169 was dissolved in 20 ml of acetone, 1.3 g of methyl iodide was added to the solution and the reaction mixture was refluxed for 15 minutes in a water bath. Compound 170 was then precipitated by the addition of ether. Amorphous product. Yield: 81%.

N-α-(8-quinolinesulfonyl)-3-amidino-(D,L)-phenylalanine-4-methylpiperidide hydroiodide (171)

0.9 g of the methyl-thioimide carboxylate 170 was converted and worked up as described in example 2 (32–34). Yield: 81%, mp from 135° C.

EXAMPLE 15

N-α-(8-quinolinesulfonyl)-3-amidino-(D,L)-phenylalanyl-piperidine-carboxylic acids (180, 181, Table 15)

N-α-(8-quinolinesulfonyl)-3-cyano-(D,L)-phenylalanyl-ethyl-piperidine-carboxylate (172, 173, Table 15)

5 mmoles of compound 167 and 7.5 mmoles of the corresponding piperidine carboxylate were coupled and worked up according to procedure A (example 3). The purification of compounds 172 and 173 was achieved by column chromatography over silica gel 60 with chloroform as the eluent.

N-α-(8-quinolinesulfonyl)-3-cyano-(D,L)-phenylalanyl-piperidine-carboxylic acids (174, 175, Table 15)

4 mmoles each of the carboxylates 172 and 173 were saponified as described in example 3 (50–60). In the work up, the reaction mixtures were adjusted to pH 4 with a 10% citric acid solution, kept in the refrigerator for some hours and the formed precipitates were filtered off. The purification of the carboxylic acids 174 and 175 was achieved by column chromatography over silica gel 60 with chloroform/methanol 90:10 as eluent.

Thioamides (176, 177, Table 15)

1.0 g each of compounds 174 and 175 was converted and worked up as described in example 2 (19–24).

Methyl-thioimide carboxylate hydroiodides (718, 179, Table 15).

The synthesis of compounds 178 and 179 was carried out by converting 0.8 g each of the thioamides 176 and 177 and working up as described in example 3 (72–82).

N-α-(8-quinolinesulfonyl)-3-amidino-(D,L)-phenylalanyl-piperidine-carboxylic acid hydroiodides (180, 181, Table 15)

0.5 g each of the methyl-thioimide carboxylate hydroiodides 178 and 179 was converted and worked up as described in example 2 (32–34).

TABLE 15

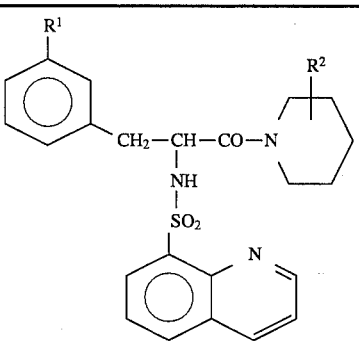

| No | SC | $R^1$ | $R^2$ | Position $R^2$ | Y (%) | mp (°C.) |
|---|---|---|---|---|---|---|
| 172 | 167 | —CN | —COOC$_2$H$_5$ | 2 | 79 | amorphous |
| 173 | 167 | —CN | —COOC$_2$H$_5$ | 4 | 70 | amorphous |
| 174 | 172 | —CN | —COOH | 2 | 73 | from 128 |
| 175 | 173 | —CN | —COOH | 4 | 60 | from 142 |
| 176 | 174 | 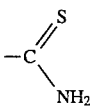 | —COOH | 2 | 86 | amorphous |
| 177 | 175 | " | —COOH | 4 | 86 | amorphous |

TABLE 15-continued

| No | SC | R¹ | R² | Position R² | Y (%) | mp (°C.) |
|---|---|---|---|---|---|---|
| 178 | 176 | −C(SCH₃)=NH ·HI | −COOH | 2 | 57 | amorphous |
| 179 | 177 | " | −COOH | 4 | 66 | amorphous |
| 180 | 178 | −C(NH)=NH₂ ·HI (NH/NH₂) | −COOH | 2 | 75 | from 168 |
| 181 | 179 | " | −COOH | 4 | 72 | from 175 |

EXAMPLE 16

N-α-(2-Naphthylsulfonyl)-3-aminomethyl-(D,L)-phenylalanyl-4-methylpiperidide (182), (D,L)-pipecolic acid (185) and -ethyl-pipecolinate (183), isonipecotic acid (186) and -ethyl-isonipecotate (184) (Table 16)

N-α-(2-Naphthylsulfonyl)-3-aminomethyl-(D,L)-phenylalanyl-4-methylpiperidide, -(D,L)-ethyl-pipecolinate and -ethyl-isonipecotate hydrochlorides (182–184, Table 16)

2.0 g of compounds 14, 39 and 41 were dissolved each in 40 ml of a mixture of dioxane/methanol 1:1 by heating, the solutions were mixed with 5 g of Raney-Nickel catalyst and 10 ml of 1N ethanolic ammonia solution and hydrogenated under normal conditions, whereby the calculated hydrogen quantity was absorbed after about 45 minutes. It was then filtered off from the catalyst, washed with 100 ml of methanol and the solvent was evaporated under reduced pressure. The oily residues were dissolved in 5 ml of methanol, acidified with 2N ethyl acetate/HCl and the hydrochlorides 182, 183 and 184 were precipitated by the addition of ether.

N-α-(2-Naphthylsulfonyl)-3-aminomethyl-(D,L)-phenylalanyl-(D,L)-pipecolic acid- and -isonipecotic acid hydrochloride (185, 186, Table 16)

0.8 g of the ethyl-carboxylate hydrochlorides 183 and 184 was dissolved in 20 ml of 0.36N methanolic potash lye and the solutions were stirred at room temperature until complete saponification had taken place (checked by TLC). The solutions were then acidified with 2N ethyl acetate/HCl, 20 ml of ether were added and the precipitated potassium chloride was filtered off. Compounds 185 and 186 were precipitated from the filtrates by the addition of a large volume of ether.

TABLE 16

| No | SC | R | Position R | Y (%) | mp (°C.) |
|---|---|---|---|---|---|
| 182 | 14 | −CH₃ | 4 | 52 | 273–275 |
| 183 | 39 | −COOC₂H₅ | 2 | 59 | from 105 |
| 184 | 41 | −COOC₂H₅ | 4 | 86 | 204–208 |
| 185 | 183 | −COOH | 2 | 76 | from 115 |
| 186 | 184 | −COOH | 4 | 76 | 155–162 |

EXAMPLE 17

Compounds with oxamidine structure (187–190, Table 17)

1.0 g each of compounds 27, 72, 74 and 132 was dissolved or suspended, respectively, in 20 ml of methanol and a 3-molar quantity of hydroxylammonium acetate was added to the reaction mixtures which were stirred for 2 hours at room temperature. It was then filtered off, the solvent was evaporated under reduced pressure, the residues were dissolved in 3–4 ml of abs. ethanol and the oxamidine hydroiodides 187–190 were precipitated by the addition of ether.

TABLE 17

[Structure: benzene ring with C(=NH)(NHOH)·HI substituent and CH₂—CH(NH—SO₂—naphthyl)—CO—R substituent]

| No | SC | R | Y (%) | mp (°C.) |
|---|---|---|---|---|
| 187 | 27 | —N(piperidinyl)—CH₃ | 59 | from 105 |
| 188 | 72 | —N(piperidinyl with COOH) | 73 | from 122 |
| 189 | 74 | —N(piperidinyl)—COOH | 71 | from 126 |
| 190 | 132 | —N(tetrahydroisoquinoline with HOOC) | 83 | from 112 |

The following compounds were synthesized in this way:
N-α-(2-Naphthylsulfonyl)-3-oxamidino-(D,L)-phenylalanine-4-methylpiperidide hydroiodide (187)

N-α-(2-Naphthylsulfonyl)-3-oxamidino-(D,L)-phenylalanyl-(D,L)-pipecolic acid hydroiodide (188), N-α-(2-Naphthylsulfonyl)-3-oxamidino-(D,L)-phenylalanyl-isonipecotic acid hydroiodide (189)

N-α-(2-Naphthylsulfonyl)-3-oxamidino-(D,L)-phenylalanyl-1,2,3,4-tetrahydroisoquinoline-3-carboxylic acid hydroiodide (190).

EXAMPLE 18

N-α-(2-Naphthylsulfonyl)-3-amino-(D,L)-phenylalanyl-piperidide (202), -4-methylpiperidide (203), -(D,L)-pipecolic acid (204), -isonipecotic acid (205) and -1,2,3,4-tetrahydroisoquinoline-3-carboxylic acid (206)

(3-Nitrobenzyl)-diethyl-acetamidomalalonate (191)

11.0 g of 3-nitrobenzyl bromide and 11.0 g of diethylacetamidomalonate were dissolved in 80 ml of abs. dioxane. A solution of 1.15 g of sodium in 20 ml of abs. ethanol was added to the above solution under stirring. The mixture was heated for 4 hours in a boiling water bath and 500 ml of water were added after cooling. The formed precipitate was filtered off, washed with water and crystallized from methanol/water. Yield: 80%, mp 153°–154° C.

3-Nitro-(D,L)-phenylalanine hydrochloride (192)

14 g of compound 191 were refluxed in a mixture of 26 ml of acetic acid and 26 ml of 6N HCl for 4 hours. The major part of compound 192 crystallized during cooling. The crystals were filtered off and dried. The filtrate was concentrated under reduced pressure, whereby an additional amount of compound 192 precipitated. The two fractions obtained were dissolved in methanol and compound 192 was precipitated by the addition of ether. The formed precipitate was filtered off, washed with ether and dried. Yield: 75%, mp 247°–248° C.

N-α-2-Naphthylsulfonyl)-3-nitro-(D,L)-phenylalanine (193)

19.8 g of compound 192 were dissolved in 252 ml of 1N KOH and reacted with a solution of 20 g of 2-naphthylsulfonyl chloride in 240 ml of ether and worked up as described in example 1 (3). Crystallization was achieved from methanol/water. Yield: 71%, mp 173°–174° C.

N-α-(2-Naphthylsulfonyl)-3-nitro-(D,L)-phenylalanyl compounds (194–201)

N-α-(2-Naphthylsulfonyl)-3-nitro-(D,L)-phenylalanine piperidides (194, 195)

7.5 mmoles of piperidine or 4-methylpiperidine, respectively, and 5 mmoles of NMM were dissolved in 10 ml of abs. dioxane, a solution of 5 mmoles of the acid chloride obtained from compound 193 and thionyl chloride in 10 ml of abs. dioxane was added dropwise and the reaction mixture was stirred for 2 hours at room temperature, whereby compounds 194 and 195 precipitated. The residue was then filtered off, washed with 50% methanol and dried.

N-α-(2-Naphthylsulfonyl)-3-nitro-(D,L)-phenylalanyl-carboxylates (196–198)

5 mmoles of compound 193 and 6 mmoles each of ethyl-(D,L)-pipecolinate, ethyl-isonipecotate as well as 1,2,3,4-tetrahydroisoquinoline-3-carboxylic acid methyl ester were coupled respectively and worked up according to procedure A (example 3). Purification was achieved by column chromatography over silica gel 60 with chloroform as the eluent.

N-α-(2-Naphthylsulfonyl)-3-nitro-(D,L)-phenylalanyl-carboxylic acids (199–201)

5 mmoles each of compounds 196–198 were saponified as described in example 3 (50–60). The isolated products were used in the next reduction step as obtained.

Amino compounds (202–206)

3 mmoles each of the nitro compounds 194, 195 and 199–201 were dissolved in a necessary volume of DMF, the solutions were mixed with a suspension of 0.4 g of Pd/C (10%) in 10 ml of ethanol and 0.5 ml of acetic acid and hydrogenated under normal conditions until the calculated hydrogen quantity was absorbed. The catalyst was then filtered off, the solvent was evaporated under reduced pressure and the obtained crude products were purified by column chromatography over silica gel 60 with chloroform/ methanol 90:10 as eluent.

The amino compounds 204 and 205 inclined to a stronger discoloration were converted into hydrochlorides as described in example 3 (83–93).

TABLE 18

Structure: 3-R¹-C₆H₄-CH₂-CH(NH-SO₂-2-naphthyl)-CO-R²

| No | SC | R¹ | R² | Y (%) | mp (°C.) |
|---|---|---|---|---|---|
| 194 | 193 | NO₂ | piperidin-1-yl | 85 | 238–240 |
| 195 | 193 | NO₂ | 4-methylpiperidin-1-yl | 95 | 182–184 |
| 196 | 193 | NO₂ | 2-(COOC₂H₅)piperidin-1-yl | 60 | 172–176 |
| 197 | 193 | NO₂ | 4-(COOC₂H₅)piperidin-1-yl | 93 | 161–163 |
| 198 | 193 | NO₂ | 3-(H₃COOC)-1,2,3,4-tetrahydroisoquinolin-2-yl | 67 | 121–127 |
| 199 | 196 | NO₂ | 2-(COOH)piperidin-1-yl | 82 | amorphous |
| 200 | 197 | NO₂ | 4-(COOH)piperidin-1-yl | 98 | amorphous |
| 201 | 198 | NO₂ | 3-(HOOC)-1,2,3,4-tetrahydroisoquinolin-2-yl | 92 | amorphous |
| 202 | 194 | NH₂ | piperidin-1-yl | 59 | 148–150 |
| 203 | 195 | NH₂ | 4-methylpiperidin-1-yl | 72 | amorphous |

TABLE 18-continued

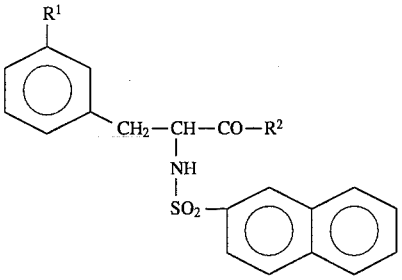

| No | SC | R¹ | R² | Y (%) | mp (°C.) |
|---|---|---|---|---|---|
| 204 | 199 | NH₂.HCl | 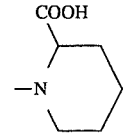 COOH | 65 | from 153 |
| 205 | 200 | NH₂.HCl | 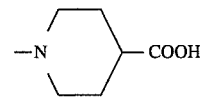 COOH | 82 | 112–115 |
| 206 | 201 | NH₂ | 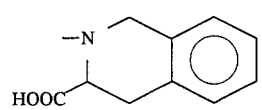 | 72 | from 150 |

EXAMPLE 19

Compounds with quanidine structure (207, 208)

N-α-(2-Naphthylsulfonyl)-3-quanidino-(D,L)-phenylalanine-piperidide hydrochloride (207)

A solution of 1.09 g of compound 202, 0.83 ml of NMM and 0.51 g of 1-amidino-3,5-dimethyl-pyrazole nitrate in 20 ml of THF was refluxed for 30 hours. After evaporation of the solvent under reduced pressure, the obtained crude product was purified by column chromatography over silica gel 60 with chloroform/methanol 95:5 as eluent. Yield: 28%, mp from 122° C.

It was converted into the hydrochloride as described in example 3 (83–93). Yield: 83%, mp from 110° C.

N-α-(2-Naphthylsulfonyl)-3-guanidino-(D,L)-phenylalanine-(D,L)-pipecolic acid hydrochloride (208)

0.69 g of the free amino compound 204 was dissolved in 12 ml of THF, the solution was mixed with 0.47 ml of NMM, 0.44 g of 1-amidino-3,5-dimethyl-pyrazole nitrate and the reaction mixture was refluxed for 50 hours. After evaporation of the solvent under reduced pressure, the obtained crude product was purified by column chromatography over silica gel 60 with chloroform/methanol 75:25 as eluent. The isolated guanidine compound was converted into the hydrochloride 208 as described in example 3 (83–93). Yield: 40%, mp from 100° C.

LIST OF ELEMENTARY ANALYSES and TLC DATA

| No | FORMULA | Mol. wt. | | C | H | N | S | TLC $R_f$ (SS) |
|---|---|---|---|---|---|---|---|---|
| 1 | $C_{17}H_{20}N_2O_5$ | 332.361 | Calc. | 61.44 | 6.07 | 8.43 | — | 0.40(4) |
|   |   |   | Found | 61.72 | 6.11 | 8.34 | — | |
| 2 | $C_{10}H_{10}N_2O_2$ | 190.204 | Calc. | 63.15 | 5.30 | 14.73 | — | 0.31(1) |
|   |   |   | Found | 63.34 | 5.47 | 14.52 | — | |
| 3 | $C_{20}H_{16}N_2O_4S$ | 380.426 | Calc. | 63.15 | 4.24 | 7.36 | 8.43 | 0.32(3) |
|   |   |   | Found | 63.40 | 4.48 | 7.66 | 8.30 | |
| 6 | $C_{20}H_{19}N_3O_4S.HCl$ | 433.918 | Calc. | 55.36 | 4.65 | 9.68 | 7.39 | 0.36(1) |
|   |   |   | Found | 54.89 | 5.09 | 9.32 | 7.42 | |
| 7 | $C_{21}H_{21}N_3O_4S.HCl$ | 447.945 | Calc. | 56.31 | 4.95 | 9.38 | 7.16 | 0.53(3) |
|   |   |   | Found | 55.98 | 5.10 | 9.22 | 7.65 | |
| 8 | $C_{23}H_{25}N_3O_4S.HCl$ | 475.999 | Calc. | 58.04 | 5.51 | 8.83 | 6.74 | 0.55(1) |
|   |   |   | Found | 57.63 | 5.61 | 8.84 | 6.72 | |
| 9 | $C_{24}H_{27}N_3O_4S.HCl$ | 490.026 | Calc. | 58.83 | 5.76 | 8.58 | 6.54 | 0.55(1) |
|   |   |   | Found | 58.89 | 5.92 | 8.58 | 6.70 | |
| 10 | $C_{27}H_{25}N_3O_4S.HCl.$ $0.5H_2O$ | 533.051 | Calc. | 60.83 | 5.11 | 7.88 | 6.02 | 0.63(1) |
|   |   |   | Found | 60.54 | 5.60 | 8.17 | 6.22 | |

LIST OF ELEMENTARY ANALYSES and TLC DATA

| No | FORMULA | Mol. wt. | | C | H | N | S | TLC $R_f$ (SS) |
|---|---|---|---|---|---|---|---|---|
| 11 | $C_{28}H_{27}N_3O_4S \cdot HCl \cdot 0.5H_2O$ | 547.078 | Calc. | 61.47 | 5.34 | 7.68 | 5.86 | 0.64(1) |
| | | | Found | 61.66 | 5.16 | 7.81 | 5.71 | |
| 12 | $C_{26}H_{27}N_3O_3S$ | 461.587 | Calc. | 67.65 | 5.90 | 9.10 | 6.95 | 0.76(3) |
| | | | Found | 67.58 | 5.75 | 9.22 | 6.72 | |
| 13 | $C_{26}H_{27}N_3O_3S$ | 461.589 | Calc. | 67.65 | 5.90 | 9.10 | 6.95 | 0.76(3) |
| | | | Found | 67.82 | 5.91 | 9.08 | 6.85 | |
| a 14 | $C_{26}H_{27}N_3O_3S$ | 461.587 | Calc. | 67.65 | 5.90 | 9.10 | 6.95 | 0.76(3) |
| | | | Found | 67.73 | 5.91 | 9.13 | 7.03 | |
| 15 | $C_{25}H_{26}N_4O_3S$ | 462.575 | Calc. | 64.91 | 5.67 | 12.11 | 6.93 | 0.21(2) |
| | | | Found | 65.08 | 5.70 | 12.11 | 6.98 | |
| 16 | $C_{30}H_{28}N_4O_3S$ | 524.646 | Calc. | 68.68 | 5.38 | 10.68 | 6.11 | 0.58(2) |
| | | | Found | 68.38 | 5.70 | 10.70 | 6.34 | |
| 17 | $C_{27}H_{28}N_4O_5S$ | 520.613 | Calc. | 62.29 | 5.42 | 10.76 | 6.16 | 0.69(3) |
| | | | Found | 62.78 | 5.73 | 10.38 | 6.28 | |
| 18 | $C_{29}H_{32}N_4O_5S$ | 548.667 | Calc. | 63.48 | 5.88 | 10.21 | 5.84 | 0.88(3) |
| | | | Found | 63.71 | 5.88 | 10.33 | 5.82 | |
| 32 | $C_{26}H_{30}N_4O_3S \cdot HI$ | 606.531 | Calc. | 51.49 | 5.15 | 9.24 | 5.29 | 0.54(1) |
| | | | Found | 51.63 | 5.23 | 9.16 | 5.16 | |
| 33 | $C_{26}H_{30}N_4O_3S \cdot HI$ | 606.531 | Calc. | 51.49 | 5.15 | 9.24 | 5.29 | 0.54(1) |
| | | | Found | 51.32 | 5.31 | 9.32 | 5.32 | |
| 34 | $C_{26}H_{30}N_4O_3S \cdot HI$ | 606.531 | Calc. | 51.49 | 5.15 | 9.24 | 5.29 | 0.46(1) |
| | | | Found | 51.40 | 5.05 | 9.30 | 5.40 | |
| 35 | $C_{25}H_{29}N_5O_3S \cdot 2HCl$ | 552.528 | Calc. | 54.35 | 5.66 | 12.68 | 5.80 | 0.08(1) |
| | | | Found | 54.73 | 5.52 | 12.58 | 5.93 | |
| 36 | $C_{30}H_{31}N_5O_3S \cdot HCl$ | 578.138 | Calc. | 62.33 | 5.58 | 12.11 | 5.55 | 0.44(1) |
| | | | Found | 62.21 | 5.61 | 11.87 | 5.70 | |
| 37 | $C_{27}H_{31}N_5O_5S \cdot HI$ | 665.557 | Calc. | 48.73 | 4.85 | 10.52 | 4.82 | 0.36(1) |
| | | | Found | 48.18 | 4.99 | 10.12 | 4.93 | |
| 38 | $C_{29}H_{35}N_5O_5S \cdot HI$ | 693.611 | Calc. | 50.22 | 5.23 | 10.10 | 4.62 | 0.45(1) |
| | | | Found | 49.97 | 5.14 | 10.08 | 4.92 | |
| 39 | $C_{28}H_{29}N_3O_5S$ | 519.625 | Calc. | 64.72 | 5.63 | 8.09 | 6.17 | 0.88(3) |
| | | | Found | 64.70 | 5.66 | 8.11 | 6.16 | |
| 40 | $C_{28}H_{29}N_3O_5S$ | 519.625 | Calc. | 64.72 | 5.63 | 8.09 | 6.17 | 0.86(3) |
| | | | Found | 64.30 | 5.66 | 8.37 | 6.32 | |
| 41 | $C_{28}H_{29}N_3O_5S$ | 519.625 | Calc. | 64.72 | 5.63 | 8.09 | 6.17 | 0.86(3) |
| | | | Found | 64.70 | 5.66 | 8.08 | 6.30 | |
| 42 | $C_{28}H_{29}N_3O_5S$ | 519.625 | Calc. | 64.72 | 5.63 | 8.09 | 6.17 | 0.83(3) |
| | | | Found | 64.37 | 5.32 | 7.82 | 6.30 | |
| 43 | $C_{29}H_{31}N_3O_5S$ | 533.652 | Calc. | 65.27 | 5.86 | 7.87 | 6.01 | 0.39(4) |
| | | | Found | 65.20 | 5.92 | 8.01 | 6.32 | |
| 44 | $C_{31}H_{35}N_3O_5S$ | 561.706 | Calc. | 66.29 | 6.28 | 7.48 | 5.71 | 0.82(3) |
| | | | Found | 66.70 | 6.53 | 7.59 | 5.81 | |
| 45 | $C_{28}H_{29}N_3O_5S$ | 519.625 | Calc. | 64.72 | 5.63 | 8.09 | 6.17 | 0.89(3) |
| | | | Found | 64.94 | 5.48 | 8.12 | 6.32 | |
| 46 | $C_{28}H_{29}N_3O_5S$ | 519.625 | Calc. | 64.72 | 5.63 | 8.09 | 6.17 | 0.84(3) |
| | | | Found | 64.60 | 5.50 | 8.24 | 6.48 | |
| 47 | $C_{29}H_{31}N_3O_5S$ | 533.652 | Calc. | 65.27 | 5.86 | 7.87 | 6.01 | 0.79(3) |
| | | | Found | 65.51 | 5.75 | 8.16 | 6.19 | |
| 48 | $C_{29}H_{31}N_3O_5S$ | 533.652 | Calc. | 65.27 | 5.86 | 7.87 | 6.01 | 0.77(3) |
| | | | Found | 65.13 | 5.25 | 8.00 | 6.18 | |
| 49 | $C_{29}H_{29}N_3O_7S$ | 563.636 | Calc. | 61.80 | 5.19 | 7.46 | 5.69 | 0.78(3) |
| | | | Found | 62.39 | 5.14 | 7.77 | 5.75 | |
| 50 | $C_{26}H_{25}N_3O_5S$ | 491.571 | Calc. | 63.53 | 5.13 | 8.55 | 6.52 | 0.58(3) |
| | | | Found | 63.22 | 5.15 | 8.39 | 6.56 | 0.54 |
| 51 | $C_{26}H_{25}N_3O_5S$ | 491.571 | Calc. | 63.53 | 5.13 | 8.55 | 6.52 | 0.58(3) |
| | | | Found | 63.26 | 5.20 | 8.34 | 6.55 | |
| 52 | $C_{26}H_{25}N_3O_5S$ | 491.571 | Calc. | 63.53 | 5.13 | 8.55 | 6.52 | 0.58(3) |
| | | | Found | 62.98 | 5.27 | 8.56 | 6.28 | |
| 53 | $C_{27}H_{27}N_3O_5S \cdot 2H_2O$ | 541.630 | Calc. | 59.87 | 5.77 | 7.76 | 5.92 | 0.52(3) |
| | | | Found | 59.93 | 5.75 | 7.88 | 5.98 | 0.48 |
| 54 | $C_{28}H_{29}N_3O_5S$ | 519.625 | Calc. | 64.72 | 5.63 | 8.09 | 6.17 | 0.54(3) |
| | | | Found | 64.58 | 5.39 | 8.36 | 6.23 | 0.51 |
| 55 | $C_{30}H_{33}N_3O_5S$ | 547.679 | Calc. | 65.79 | 6.07 | 7.67 | 5.85 | 0.52(3) |
| | | | Found | 65.69 | 6.13 | 7.52 | 5.53 | 0.48 |
| 56 | $C_{27}H_{27}N_3O_5S$ | 505.598 | Calc. | 64.14 | 5.38 | 8.31 | 6.34 | 0.68(3) |
| | | | Found | 64.32 | 5.52 | 8.33 | 6.68 | 0.65 |
| 57 | $C_{27}H_{27}N_3O_5S$ | 505.598 | Calc. | 64.14 | 5.38 | 8.31 | 6.34 | 0.58(3) |
| | | | Found | 63.52 | 5.72 | 7.98 | 6.18 | |
| 58 | $C_{28}H_{29}N_3O_5S$ | 519.625 | Calc. | 64.72 | 5.63 | 8.09 | 6.17 | 0.50(3) |
| | | | Found | 64.97 | 5.77 | 8.23 | 6.60 | |
| 59 | $C_{27}H_{27}N_3O_5S$ | 505.598 | Calc. | 64.14 | 5.38 | 8.31 | 6.34 | 0.60(3) |
| | | | Found | 63.91 | 5.30 | 8.21 | 6.61 | |
| 60 | $C_{27}H_{25}N_3O_7S \cdot H_2O \cdot HCl$ | 553.598 | Calc. | 58.58 | 4.92 | 7.59 | 5.79 | 0.23(3) |
| | | | Found | 58.81 | 4.62 | 8.03 | 6.12 | |
| 83 | $C_{26}H_{28}N_4O_5S \cdot H_2O$ | 563.079 | Calc. | 55.46 | 5.55 | 9.95 | 5.69 | 0.42(1) |

-continued

LIST OF ELEMENTARY ANALYSES and TLC DATA

| No | FORMULA | Mol. wt. | | C | H | N | S | TLC $R_f$ (SS) |
|---|---|---|---|---|---|---|---|---|
| | | | Found | 55.96 | 5.90 | 9.71 | 5.36 | 0.37 |
| 84 | $C_{26}H_{28}N_4O_5S \cdot HCl$ | 545.063 | Calc. | 57.29 | 5.36 | 10.28 | 5.88 | 0.38(1) |
| | | | Found | 56.89 | 5.56 | 10.01 | 6.17 | |
| 85 | $C_{26}H_{28}N_4O_5S \cdot HCl$ | 545.063 | Calc. | 57.29 | 5.36 | 10.28 | 5.88 | 0.35(1) |
| | | | Found | 56.85 | 5.60 | 10.02 | 6.38 | |
| 86 | $C_{27}H_{30}N_4O_5S \cdot HCl$ | 559.090 | Calc. | 58.00 | 5.59 | 10.02 | 5.74 | 0.41(1) |
| | | | Found | 58.72 | 5.86 | 9.85 | 5.82 | 0.35 |
| 87 | $C_{28}H_{32}N_4O_5S \cdot HCl$ | 573.117 | Calc. | 58.68 | 5.80 | 9.98 | 5.59 | 0.44(1) |
| | | | Found | 58.77 | 6.01 | 9.68 | 5.88 | |
| 88 | $C_{30}H_{36}N_4O_5S \cdot HCl$ | 601.171 | Calc. | 59.94 | 6.20 | 9.311 | 5.33 | 0.50(1) |
| | | | Found | 59.61 | 6.37 | 9.28 | 5.68 | 0.45 |
| 89 | $C_{27}H_{30}N_4O_5S \cdot HCl \cdot H_2O$ | 577.106 | Calc. | 56.19 | 5.76 | 9.71 | 5.56 | 0.57(1) |
| | | | Found | 56.22 | 5.66 | 9.80 | 5.81 | 0.53 |
| 90 | $C_{27}H_{30}N_4O_5S \cdot HCl \cdot H_2O$ | 577.106 | Calc. | 56.19 | 5.76 | 9.71 | 5.56 | 0.41(1) |
| | | | Found | 56.18 | 5.67 | 9.62 | 5.52 | |
| 91 | $C_{28}H_{32}N_4O_5 \cdot HCl$ | 573.117 | Calc. | 58.68 | 5.80 | 9.78 | 5.59 | 0.49(1) |
| | | | Found | 58.49 | 5.78 | 9.57 | 6.03 | |
| 92 | $C_{27}H_{30}N_4O_5S \cdot HCl \cdot H_2O$ | 577.106 | Calc. | 56.19 | 5.76 | 9.71 | 5.56 | 0.48(1) |
| | | | Found | 55.96 | 5.50 | 9.52 | 5.36 | |
| 93 | $C_{27}H_{28}N_4O_7S \cdot HCl \cdot 0.5H_2O$ | 598.082 | Calc. | 54.22 | 5.06 | 9.37 | 5.36 | 0.34(1) |
| | | | Found | 54.00 | 4.96 | 9.44 | 5.77 | |
| 94 | $C_{27}H_{30}N_4O_5S \cdot HCl \cdot H_2O$ | 577.106 | Calc. | 56.19 | 5.76 | 9.71 | 5.56 | 0.47(1) |
| | | | Found | 55.96 | 5.90 | 9.71 | 5.36 | |
| 95 | $C_{27}H_{30}N_4O_5S \cdot HCl$ | 559.090 | Calc. | 58.00 | 5.59 | 10.02 | 5.74 | 0.43(1) |
| | | | Found | 57.58 | 5.63 | 9.67 | 5.97 | |
| 96 | $C_{27}H_{30}N_4O_5S \cdot HCl$ | 559.090 | Calc. | 58.00 | 5.59 | 10.02 | 5.74 | 0.40(1) |
| | | | Found | 57.54 | 5.58 | 9.79 | 5.48 | |
| 97 | $C_{28}H_{32}N_4O_5S \cdot HCl$ | 573.119 | Calc. | 58.68 | 5.80 | 9.78 | 5.59 | 0.55(1) |
| | | | Found | 58.72 | 5.86 | 9.54 | 5.58 | |
| 98 | $C_{29}H_{34}N_5O_5S \cdot HCl$ | 587.144 | Calc. | 59.32 | 6.01 | 9.54 | 5.46 | 0.53(1) |
| | | | Found | 59.23 | 6.23 | 9.61 | 5.56 | |
| 99 | $C_{28}H_{32}N_4O_5S \cdot HCl \cdot H_2O$ | 591.133 | Calc. | 56.89 | 5.97 | 9.48 | 5.42 | 0.59(1) |
| | | | Found | 56.72 | 5.53 | 9.58 | 5.70 | |
| 100 | $C_{27}H_{32}N_4O_5S \cdot HCl \cdot H_2O$ | 591.133 | Calc. | 56.89 | 5.97 | 9.48 | 5.42 | 0.48(1) |
| | | | Found | 56.60 | 5.82 | 9.14 | 5.19 | |
| 101 | $C_{28}H_{32}N_4O_5S \cdot HCl \cdot H_2O$ | 591.133 | Calc. | 56.89 | 5.97 | 9.48 | 5.42 | 0.55(1) |
| | | | Found | 56.87 | 5.83 | 9.45 | 5.30 | |
| 102 | $C_{32}H_{36}N_4O_6S$ | 604.732 | Calc. | 63.56 | 6.00 | 9.26 | 5.30 | 0.60(3) |
| | | | Found | 63.66 | 6.14 | 9.39 | 5.54 | |
| 103 | $C_{33}H_{38}N_4O_6S$ | 618.759 | Calc. | 64.06 | 6.19 | 9.05 | 5.18 | 0.34(3) |
| | | | Found | 64.13 | 6.21 | 9.16 | 5.45 | |
| 104 | $C_{30}H_{32}N_4O_6S$ | 576.678 | Calc. | 62.48 | 5.59 | 9.72 | 5.56 | 0.28(3) |
| | | | Found | 62.13 | 5.73 | 9.63 | 5.72 | |
| 105 | $C_{32}H_{36}N_4O_6S \cdot H_2O$ | 622.748 | Calc. | 61.72 | 6.15 | 9.00 | 5.15 | 0.15(3) |
| | | | Found | 61.23 | 6.62 | 8.83 | 5.18 | |
| 110 | $C_{30}H_{35}N_5O_6S \cdot HI$ | 721.622 | Calc. | 49.93 | 5.03 | 9.71 | 4.44 | 0.32(1) |
| | | | Found | 50.14 | 5.20 | 9.79 | 4.62 | |
| 111 | $C_{32}H_{39}N_5O_6S \cdot HI$ | 749.676 | Calc. | 51.27 | 5.38 | 9.34 | 4.28 | 0.30(1) |
| | | | Found | 51.59 | 5.35 | 9.64 | 4.30 | |
| 112 | $C_{32}H_{36}N_4O_6S$ | 604.732 | Calc. | 63.56 | 6.00 | 9.26 | 5.30 | 0.79(3) |
| | | | Found | 63.25 | 6.58 | 9.74 | 4.92 | |
| 115 | $C_{32}H_{39}N_6O_6S \cdot HI \cdot 1.5H_2O$ | 776.700 | Calc. | 49.49 | 5.58 | 9.02 | 4.13 | 0.51(1) |
| | | | Found | 49.08 | 5.36 | 9.17 | 4.36 | |
| 116 | $C_{28}H_{31}N_5O_6S \cdot HCl \cdot 0.5H_2O$ | 611.124 | Calc. | 55.03 | 5.44 | 11.46 | 5.25 | 0.29(1) |
| | | | Found | 55.04 | 5.78 | 10.89 | 5.11 | |
| 117 | $C_{29}H_{33}N_6O_6S \cdot HCl \cdot H_2O$ | 634.159 | Calc. | 54.93 | 5.72 | 11.04 | 5.06 | 0.33(1) |
| | | | Found | 54.77 | 5.58 | 10.88 | 5.15 | |
| 118 | $C_{29}H_{31}N_3O_5S$ | 533.652 | Calc. | 65.27 | 5.86 | 7.87 | 6.01 | 0.68(2) |
| | | | Found | 65.29 | 5..81 | 7.89 | 6.54 | |
| 119 | $C_{29}H_{31}N_3O_5S$ | 533.652 | Calc. | 65.27 | 5.86 | 7.87 | 6.01 | 0.58(2) |
| | | | Found | 65.39 | 6.17 | 8.21 | 5.83 | |
| 123 | $C_{25}H_{26}N_4O_5S$ (Betain) | 512.591 | Calc. | 58.58 | 5.51 | 10.93 | 6.26 | 0.30(1) |
| | | | Found | 58.42 | 5.97 | 10.50 | 5.98 | |
| 124 | $C_{26}H_{28}N_4O_5S \cdot HCl \cdot H_2O$ | 563.080 | Calc. | 55.46 | 5.55 | 9.95 | 5.69 | 0.38(1) |
| | | | Found | 55.62 | 5.75 | 9.74 | 5.83 | |
| 125 | $C_{10}H_{10}N_2O_2 \cdot HCl$ | 226.665 | Calc. | 52.99 | 4.89 | 12.36 | — | 0.31(1) |
| | | | Found | 53.03 | 5.04 | 12.13 | — | |
| 126 | $C_{20}H_{16}N_2O_4S \cdot 0.5H_2O$ | 389.434 | Calc. | 61.68 | 4.40 | 7.19 | 8.23 | 0.33(3) |
| | | | Found | 61.39 | 4.31 | 6.94 | 8.57 | |
| 127 | $C_{29}H_{31}N_3O_5S$ | 533.652 | Calc. | 65.27 | 5.86 | 7.87 | 6.01 | 0.58(2) |
| | | | Found | 65.49 | 6.03 | 8.15 | 5.92 | |
| 128 | $C_{31}H_{27}N_3O_5S$ | 553.642 | Calc. | 67.25 | 4.92 | 7.59 | 5.79 | 0.88(3) |
| | | | Found | 67.25 | 5.33 | 7.39 | 5.49 | |
| 129 | $C_{30}H_{25}N_3O_5S$ | 539.615 | Calc. | 66.78 | 4.67 | 7.79 | 5.94 | 0.61(3) |
| | | | Found | 66.78 | 4.67 | 7.58 | 5.94 | |

LIST OF ELEMENTARY ANALYSES and TLC DATA

| No | FORMULA | Mol. wt. | | C | H | N | S | TLC $R_f$ (SS) |
|---|---|---|---|---|---|---|---|---|
| 134 | $C_{40}H_{28}N_4O_5S \cdot HI$ | 684.559 | Calc. | 52.64 | 4.27 | 8.18 | 4.68 | 0.42(1) |
| | | | Found | 52.94 | 4.53 | 8.62 | 4.82 | 0.39 |
| 135 | $C_{31}H_{30}N_4O_5S \cdot HI$ | 698.586 | Calc. | 53.30 | 4.47 | 8.02 | 4.59 | 0.54(1) |
| | | | Found | 53.53 | 4.77 | 7.70 | 5.04 | |
| 136 | $C_{27}H_{29}N_3O_5S$ | 507.614 | Calc. | 63.89 | 5.76 | 8.28 | 6.32 | 0.84(3) |
| | | | Found | 64.07 | 5.62 | 8.33 | 6.65 | |
| 139 | $C_{27}H_{32}N_4O_5S \cdot HI$ | 652.558 | Calc. | 49.70 | 5.10 | 8.59 | 4.91 | 0.55(1) |
| | | | Found | 49.28 | 5.16 | 8.50 | 5.11 | |
| 140 | $C_{23}H_{24}N_4O_5S \cdot HCl \cdot H_2O$ | 523.014 | Calc. | 52.82 | 5.20 | 10.71 | 6.13 | 0.31(1) |
| | | | Found | 53.44 | 4.92 | 10.27 | 6.01 | |
| 141 | $C_{24}H_{26}N_4O_5S \cdot HCl \cdot 0.5 H_2O$ | 528.033 | Calc. | 54.59 | 5.35 | 10.61 | 6.07 | 0.44(1) |
| | | | Found | 54.96 | 5.41 | 10.20 | 5.96 | |
| 142 | $C_{31}H_{33}N_3O_5S$ | 559.690 | Calc. | 66.53 | 5.94 | 7.51 | 5.73 | 0.83(3) |
| | | | Found | 66.09 | 5.74 | 7.30 | 5.93 | |
| 143 | $C_{30}H_{31}N_3O_5S$ | 545.663 | Calc. | 66.04 | 5.73 | 7.70 | 5.88 | 0.65(3) |
| | | | Found | 66.42 | 5.28 | 8.12 | 5.76 | 0.62 |
| 146 | $C_{30}H_{34}N_4O_5S \cdot HI$ | 690.607 | Calc. | 52.18 | 5.11 | 8.11 | 4.64 | 0.45(1) |
| | | | Found | 52.43 | 5.25 | 8.21 | 5.06 | |
| 147 | $C_{31}H_{33}N_3O_5S$ | 559.690 | Calc. | 66.53 | 5.94 | 7.51 | 5.73 | 0.84(3) |
| | | | Found | 66.74 | 6.05 | 7.44 | 5.51 | |
| 148 | $C_{30}H_{31}N_3O_5S$ | 545.663 | Calc. | 66.04 | 5.73 | 7.70 | 5.88 | 0.56(3) |
| | | | Found | 65.83 | 5.43 | 7.49 | 5.54 | 0.49 |
| 151 | $C_{30}H_{32}N_4O_5S \cdot HCl$ | 599.155 | Calc. | 60.14 | 5.89 | 9.35 | 5.35 | 0.48(1) |
| | | | Found | 60.43 | 5.53 | 9.63 | 5.70 | 0.40 |
| 152 | $C_{22}H_{19}N_3O_5S$ | 437.479 | Calc. | 60.40 | 4.38 | 9.61 | 7.33 | 0.17(3) |
| | | | Found | 60.12 | 4.18 | 9.23 | 7.37 | |
| 153 | $C_{28}H_{30}N_4O_4S$ | 518.640 | Calc. | 64.84 | 5.83 | 10.80 | 6.18 | 0.79(3) |
| | | | Found | 64.72 | 5.85 | 11.17 | 6.22 | |
| 156 | $C_{28}H_{33}N_5O_4S \cdot HI$ | 663.584 | Calc. | 50.68 | 5.16 | 10.55 | 4.83 | 0.46(1) |
| | | | Found | 51.12 | 4.98 | 10.15 | 4.71 | |
| 157 | $C_{30}H_{32}N_4O_6S$ | 576.678 | Calc. | 62.48 | 5.59 | 9.72 | 5.56 | 0.83(3) |
| | | | Found | 62.49 | 5.61 | 9.64 | 5.62 | |
| 158 | $C_{30}H_{32}N_4O_6S$ | 576.678 | Calc. | 62.48 | 5.59 | 9.72 | 5.56 | 0.76(3) |
| | | | Found | 62.94 | 5.16 | 9.52 | 5.71 | |
| 159 | $C_{28}H_{28}N_4O_6S$ | 548.624 | Calc. | 61.30 | 5.14 | 10.21 | 5.84 | 0.57(3) |
| | | | Found | 61.78 | 4.72 | 10.53 | 5.49 | 0.40 |
| 160 | $C_{28}H_{28}N_4O_6S$ | 548.624 | Calc. | 61.30 | 5.14 | 10.21 | 5.84 | 0.53(3) |
| | | | Found | 61.52 | 4.87 | 10.43 | 5.97 | |
| 165 | $C_{28}H_{31}N_5O_6S \cdot HI$ | 693.568 | Calc. | 48.49 | 4.65 | 10.10 | 4.62 | 0.35(1) |
| | | | Found | 48.12 | 5.10 | 10.41 | 4.73 | 0.26 |
| 166 | $C_{28}H_{31}N_5O_6S \cdot HI$ | 693.568 | Calc. | 48.49 | 4.65 | 10.10 | 4.62 | 0.31(1) |
| | | | Found | 48.93 | 5.12 | 9.73 | 4.31 | |
| 167 | $C_{19}H_{15}N_3O_4S$ | 381.414 | Calc. | 59.83 | 3.96 | 11.02 | 8.41 | 0.28(3) |
| | | | Found | 59.68 | 4.44 | 11.26 | 8.68 | |
| 168 | $C_{25}H_{26}N_4O_3S$ | 462.575 | Calc. | 64.91 | 5.67 | 12.11 | 6.93 | 0.90(3) |
| | | | Found | 64.59 | 5.82 | 12.30 | 6.73 | |
| 171 | $C_{25}H_{29}N_5O_3S \cdot HI$ | 607.519 | Calc. | 49.43 | 4.98 | 11.53 | 5.28 | 0.32(1) |
| | | | Found | 49.66 | 5.17 | 11.43 | 5.61 | |
| 172 | $C_{27}H_{28}N_4O_5S$ | 520.613 | Calc. | 62.29 | 5.42 | 10.76 | 6.16 | 0.77(3) |
| | | | Found | 61.85 | 5.56 | 10.90 | 6.40 | |
| 173 | $C_{27}H_{28}N_4O_5S$ | 520.613 | Calc. | 62.29 | 5.42 | 10.76 | 6.16 | 0.83(3) |
| | | | Found | 61.58 | 5.36 | 10.68 | 6.38 | |
| 174 | $C_{25}H_{24}N_4O_5S$ | 492.559 | Calc. | 60.96 | 4.91 | 11.37 | 6.51 | 0.51(3) |
| | | | Found | 61.58 | 5.36 | 11.17 | 6.66 | 0.47 |
| 175 | $C_{25}H_{24}N_4O_5S$ | 492.559 | Calc. | 60.96 | 4.91 | 11.37 | 6.51 | 0.57(3) |
| | | | Found | 60.47 | 5.19 | 11.30 | 6.21 | |
| 180 | $C_{25}H_{27}N_5O_5S \cdot HI$ | 637.503 | Calc. | 47.10 | 4.43 | 10.99 | 5.03 | 0.40(1) |
| | | | Found | 47.58 | 4.28 | 11.31 | 5.38 | 0.34 |
| 181 | $C_{25}H_{27}N_5O_5S \cdot HI$ | 637.503 | Calc. | 47.10 | 4.43 | 10.99 | 5.03 | 0.20(1) |
| | | | Found | 47.53 | 4.78 | 11.72 | 5.43 | |
| 182 | $C_{26}H_{31}N_3O_3S \cdot HCl$ | 502.080 | Calc. | 62.20 | 6.42 | 8.37 | 6.39 | 0.43(1) |
| | | | Found | 62.64 | 6.01 | 8.78 | 6.07 | |
| 183 | $C_{28}H_{33}N_3O_5S \cdot HCl$ | 560.118 | Calc. | 60.04 | 6.12 | 7.50 | 5.72 | 0.56(1) |
| | | | Found | 59.94 | 6.43 | 7.12 | 5.97 | |
| 184 | $C_{28}H_{33}N_3O_5S \cdot HCl$ | 560.118 | Calc. | 60.04 | 6.12 | 7.50 | 5.72 | 0.41(1) |
| | | | Found | 59.80 | 6.25 | 7.87 | 5.38 | |
| 185 | $C_{26}H_{29}N_3O_5S \cdot HCl$ | 532.064 | Calc. | 58.69 | 5.68 | 7.90 | 6.03 | 0.50(1) |
| | | | Found | 58.22 | 5.99 | 7.61 | 6.34 | |
| 186 | $C_{26}H_{29}N_3O_5S \cdot HCl$ | 532.064 | Calc. | 58.69 | 5.68 | 7.90 | 6.03 | 0.32(1) |
| | | | Found | 59.12 | 5.43 | 7.64 | 6.17 | |
| 187 | $C_{26}H_{30}N_4O_4S \cdot HI$ | 622.531 | Calc. | 50.16 | 5.02 | 9.00 | 5.15 | 0.92(1) |
| | | | Found | 50.65 | 5.19 | 9.08 | 5.37 | |
| 188 | $C_{26}H_{28}N_4O_6S \cdot HI$ | 652.515 | Calc. | 47.86 | 4.48 | 8.59 | 4.91 | 0.61(1) |
| | | | Found | 48.16 | 4.83 | 8.51 | 4.95 | |
| 189 | $C_{26}H_{28}N_4O_6S \cdot HI$ | 652.515 | Calc. | 47.86 | 4.48 | 8.59 | 4.91 | 0.72(1) |

LIST OF ELEMENTARY ANALYSES and TLC DATA

| No | FORMULA | Mol. wt. | | C | H | N | S | TLC $R_f$ (SS) |
|---|---|---|---|---|---|---|---|---|
| 190 | $C_{30}H_{28}N_4O_6S \cdot HI$ | 700.559 | Found<br>Calc. | 48.24<br>51.43 | 4.67<br>4.17 | 9.01<br>8.00 | 5.23<br>4.58 | 0.71(1) |
| 191 | $C_{16}H_{20}N_2O_7$ | 352.350 | Found<br>Calc. | 50.99<br>54.54 | 4.65<br>5.72 | 8.21<br>7.95 | 4.93<br>— | 0.52(4) |
| 192 | $C_9H_{10}N_2O_4 \cdot HCl$ | 246.654 | Found<br>Calc. | 54.31<br>43.83 | 5.52<br>4.50 | 7.92<br>11.36 | —<br>— | 0.25(1) |
| 193 | $C_{19}H_{16}N_2O_6S$ | 400.415 | Found<br>Calc. | 43.91<br>56.99 | 4.52<br>4.03 | 11.28<br>7.00 | —<br>8.00 | 0.28(3) |
| 194 | $C_{24}H_{25}N_3O_5S$ | 467.549 | Found<br>Calc. | 57.17<br>61.65 | 4.28<br>5.39 | 6.97<br>8.99 | 8.32<br>6.86 | 0.67(3) |
| 195 | $C_{25}H_{27}N_3O_5S$ | 481.576 | Found<br>Calc. | 61.54<br>62.35 | 5.49<br>5.65 | 8.90<br>8.73 | 6.91<br>6.66 | 0.73(3) |
| 196 | $C_{27}H_{29}N_3O_7S$ | 539.614 | Found<br>Calc. | 62.77<br>60.10 | 6.04<br>5.42 | 9.01<br>7.79 | 6.35<br>5.94 | 0.83(3) |
| 197 | $C_{27}H_{29}N_3O_7S$ | 539.614 | Found<br>Calc. | 60.03<br>60.10 | 5.22<br>5.42 | 7.84<br>7.79 | 5.90<br>5.94 | 0.85(3) |
| 198 | $C_{30}H_{27}N_3O_7S$ | 573.631 | Found<br>Calc. | 60.07<br>62.82 | 5.43<br>4.74 | 7.97<br>7.33 | 6.20<br>5.59 | 0.85(3) |
| 199 | $C_{25}H_{25}N_3O_7S$ | 511.560 | Found<br>Calc. | 62.65<br>58.70 | 4.36<br>4.93 | 7.46<br>8.21 | 5.23<br>6.27 | 0.59(3) |
| 200 | $C_{25}H_{25}N_3O_7S$ | 511.560 | Found<br>Calc. | 59.05<br>58.70 | 4.63<br>4.93 | 8.02<br>8.21 | 6.10<br>6.27 | 0.57<br>0.61(3) |
| 201 | $C_{29}H_{25}N_3O_7S \cdot H_2O$ | 577.620 | Found<br>Calc. | 58.80<br>60.30 | 4.94<br>4.71 | 8.31<br>7.28 | 6.51<br>5.55 | 0.59(3) |
| 202 | $C_{24}H_{27}N_3O_3S$ | 437.565 | Found<br>Calc. | 60.45<br>65.88 | 4.46<br>6.22 | 7.65<br>9.60 | 6.03<br>7.33 | 0.56<br>0.28(2) |
| 203 | $C_{25}H_{29}N_3O_3S$ | 451.592 | Found<br>Calc. | 65.44<br>66.49 | 5.98<br>6.47 | 9.82<br>9.31 | 7.71<br>7.10 | 0.54(3) |
| 204 | $C_{25}H_{27}N_3O_5S \cdot HCl \cdot 1.5 H_2O$ | 545.061 | Found<br>Calc | 66.52<br>55.09 | 6.38<br>5.73 | 9.52<br>7.71 | 7.38<br>5.88 | 0.34(3) |
| 205 | $C_{25}H_{27}N_3O_5S \cdot HCl \cdot 0.5 H_2O$ | 527.045 | Found<br>Calc. | 55.34<br>56.97 | 5.91<br>5.55 | 8.31<br>7.97 | 5.88<br>6.08 | 0.30<br>0.30(3) |
| 206 | $C_{29}H_{27}N_3O_5S \cdot 2.5 H_2O$ | 574.660 | Found<br>Calc. | 56.42<br>60.61 | 5.88<br>5.61 | 7.62<br>7.31 | 5.99<br>5.58 | 0.25(3) |
| 207 | $C_{25}H_{29}N_5O_3S \cdot HCl$ | 516.067 | Found<br>Calc. | 60.32<br>58.19 | 5.23<br>5.86 | 7.45<br>13.57 | 5.05<br>6.21 | 0.46(1) |
| 208 | $C_{26}H_{29}N_5O_5S \cdot HCl \cdot 2 H_2O$ | 596.110 | Found<br>Calc. | 58.02<br>52.39 | 6.21<br>5.75 | 13.79<br>11.75 | 6.02<br>5.38 | 0.43(1) |
| | | | Found | 52.41 | 5.48 | 11.69 | 5.34 | 0.36 |

The biological properties of some representative compounds in the present invention are mentioned hereafter:

Tables 19–25 show the inhibition of the clotting enzymes thrombin and factor $X_a$ by the mentioned compounds by means of the dissociation constant $K_i$ (expressed in µmoles/l). All the compounds investigated competitively inhibit the substrate splitting caused by the two enzymes. Among the derivatives of 3-amidinophenylalanine listed in Table 19, there are a series of compounds having a high antithrombin activity, i.e. with $K_i$-values below 1 µmole/l. The thrombin inhibition is more pronounced than the inhibition of factor $X_a$. The $K_i$-values for the inhibition of factor $X_a$ are usually higher by 2 orders of magnitude than those for thrombin inhibition.

The compounds which are derived from 3-guanidinophenylalanine (Table 20), 3-oxamidinophenylalanine (Table 21), 3-aminophenylalanine (Table 22) and 3-aminomethylphenylalanine (Table 23) produce lower antithrombin activity, some of them, however, do have $K_i$-values for thrombin inhibition in the micromolar range.

When replacing the 2-naphthylsulfonyl protective group by a quinolylsulfonyl residue (Table 24) or a 2-naphthylsulfonyl glycyl residue (Table 25), respectively, compounds with an antithrombin activity in the micromolar range are also found.

TABLE 19

Inhibition of thrombin and factor $X_a$ by derivatives of N-α-(2-naphthylsulfonyl)-3-amidinophenylalanine $R^1$ = amidino, n = 0, $R^4$ = 2-naphthyl

| | | $K_i$ in µmoles/l | |
|---|---|---|---|
| Compound | $R^2$ | Thrombin | Factor $X_a$ |
| NAPAP | | 0.006 | 7.9 |
| TAPAM | | 66 | 0.84 |
| 7 | OMe | 0.28 | 2.5 |
| 123 | Pro-OH | 0.68 | 220 |
| 124 | Pro-OMe | 0.27 | 104 |
| 83 | Pip-OH | 0.26 | 38 |
| 94 | Pip-OMe | 0.07 | 46 |
| 116 | Pip-Gly-OH | 1.3 | 110 |
| 117 | Pip-Gly-OMe | 0.88 | 38 |
| 84 | Nip-OH | 1.1 | 44 |
| 95 | Nip-OMe | 0.15 | 18 |
| 85 | iNip-OH | 0.57 | 43 |
| 96 | iNip-OMe | 0.017 | 43 |
| 32 | Ppd(2-Me) | 0.13 | 74 |
| 33 | Ppd(3-Me) | 0.13 | 32 |
| 34 | Ppd(4-Me) | 0.0086 | 41 |
| 86 | Pip(4-Me)-OH | 0.12 | 96 |
| 97 | Pip(4-Me)-OMe | 0.096 | 58 |
| 35 | Pzd(4-Me) | 0.036 | 30 |
| 134 | THICH-3-COOH | 0.018 | 42 |

TABLE 19-continued

Inhibition of thrombin and factor $X_a$ by derivatives of
N-α-(2-naphthylsulfonyl)-3-amidinophenylalanine
$R^1$ = amidino, n = 0, $R^4$ = 2-naphthyl

| Compound | $R^2$ | $K_i$ in μmoles/l Thrombin | Factor $X_a$ |
|---|---|---|---|
| 151 | DHICH-3-COOH | 0.12 | 54 |

Pro-OH = proline, Pip-OH = pipecolic acid, Nip-OH = nipecotic acid, iNip-OH = isonipecotic acid, Ppd = piperidide, Pzd = piperazide, Gly = glycine, OMe = methyl ester, THICH-3-COOH = tetrahydroisoquinoline-3-carboxylic acid, DHICH-3-COOH = decahydroisoquinoline-3-carboxylic acid

TABLE 20

Inhibition of thrombin and factor $X_a$ by derivatives of
N-α-(2-naphthylsulfonyl)-3-guanidinophenylalanine
$R^1$ = guanidino, n = 0, $R^4$ = 2-naphthyl

| Compound | $R^2$ | $K_i$ in μmoles/l Thrombin | Factor $X_a$ |
|---|---|---|---|
| 208 | Pip-OH | 29 | 82 |
| 207 | Ppd | 0.40 | 107 |

TABLE 21

Inhibition of thrombin and factor $X_a$ by derivatives of
N-α-(2-naphthylsulfonyl)-3-oxamidinophenylalanine
$R^1$ = oxamidino, n = 0, $R^4$ = 2-naphthyl

| Compound | $R^2$ | $K_i$ in μmoles/l Thrombin | Factor $X_a$ |
|---|---|---|---|
| 188 | Pip-OH | 330 | 410 |
| 189 | iNip-OH | 270 | 670 |
| 187 | Ppd(4-Me) | 2.8 | >1000 |
| 190 | THICH-3-COOH | 2.4 | 130 |

TABLE 22

Inhibition of thrombin and factor $X_a$ by derivatives of
N-α-(2-naphthylsulfonyl)-3-aminophenylalanine
$R^1$ = amino, n = 0, $R^4$ = 2-naphthyl

| Compound | $R^2$ | $K_i$ in μmoles/l Thrombin | Factor $X_a$ |
|---|---|---|---|
| 204 | Pip-OH | 130 | 450 |
| 205 | iNip-OH | 720 | 720 |
| 203 | Ppd(4-Me) | 8.9 | 210 |

TABLE 23

Inhibition of thromb4Ln and factor $X_a$ by derivatives of
N-α-(2-naphthylsulfonyl)-3-aminomethylphenylalanine
$R^1$ = aminomethyl, n = 0, $R^4$ = 2-naphthyl

| Compound | $R^2$ | $K_i$ in μmoles/l Thrombin | Factor $X_a$ |
|---|---|---|---|
| 185 | Pip-OH | 50 | 140 |
| 186 | iNip-OH | 0.5 | 230 |
| 182 | Ppd(4-Me) | 1.9 | 500 |

TABLE 24

Inhibition of thrombin and factor $X_a$ by derivatives of
N-α-(8-quinolylsulfonyl)-3-amidinophenylalanine
$R^1$ = amidino, n = 0, $R^4$ = 8-quinolyl

| Compound | $R^2$ | $K_i$ in μmoles/l Thrombin | Factor $X_a$ |
|---|---|---|---|
| 180 | Pip-OH | 16 | 380 |
| 181 | iNip-OH | 127 | 260 |
| 171 | Ppd(4-Me) | 0.34 | 180 |

TABLE 25

Inhibition of thrombin and factor $X_a$ by derivatives of
N-α-(2-naphthylsulfonyl)-glycyl-3-amidinophenylalanine
$R^1$ = amidino, n = 1, $R^3$ = H, $R^4$ = 2-naphthyl

| Compound | $R^2$ | $K_i$ in μmoles/l Thrombin | Factor $X_a$ |
|---|---|---|---|
| 165 | Pip-OH | 61 | 48 |
| 166 | iNip-OH | 46 | 97 |
| 156 | Ppd(4-Me) | 3.6 | 25 |

Table 26 shows the inhibitory effect of some representative compounds in the present invention towards trypsin, plasmin, factor $XII_a$, plasma kallikrein, tPA and glandular kallikrein. Compared to thrombin, trypsin is more weakly inhibited, the $K_i$-values are higher by one order of magnitude. The effectiveness of the compounds is considerably lower towards plasmin, plasma kallikrein and factor $X_a$ ($K_i$ higher by 2 orders of magnitude). The derivatives are practically ineffective towards factor $XII_a$, tPA and glandular kallikrein. Therefore, the majority of the compounds may be called selective thrombin inhibitors.

TABLE 26

Inhibition of thrombin, trypsin, plasmin, factor Xa, factor XIIA, tPA, glandular and plasma kallikrein by selected derivatives of the present invention ($K_i$ in μmoles/l)

| Compound | $R^1$ | $R^2$ | $R^4$ | n | Thrombin | Trypsin | Plasmin | Factor Xa | Factor XIIa | tPA | Gland. Kallikrein | Plasma Kallikrein |
|---|---|---|---|---|---|---|---|---|---|---|---|---|
| NAPAP | | | | | 0.006 | 0.69 | 30 | 7.9 | 500 | 70 | 93 | 5.6 |
| TAPAM | | | | | 66 | 16 | 160 | 0.84 | 180 | 27 | 890 | 15 |
| 7 | Am | OMe | Na | 0 | 0.28 | 2.5 | 5.2 | 2.5 | 190 | 120 | 210 | 18 |

TABLE 26-continued

Inhibition of thrombin, trypsin, plasmin, factor Xa, factor XIIA, tPA, glandular and plasma kallikrein by selected derivatives of the present invention ($K_i$ in µmoles/l)

| Compound | R¹ | R² | R⁴ | n | Thrombin | Trypsin | Plasmin | Factor Xa | Factor XIIa | tPA | Gland. Kallikrein | Plasma Kallikrein |
|---|---|---|---|---|---|---|---|---|---|---|---|---|
| 123 | Am | Pro-OH | Na | 0 | 0.68 | 0.96 | 95 | 220 | >1000 | 300 | >1000 | 59 |
| 124 | Am | Pro-OMe | Na | 0 | 0.27 | 3.4 | 11 | 104 | 600 | 225 | >1000 | 29 |
| 83 | Am | Pip-OH | Na | 0 | 0.26 | 0.63 | 34 | 38 | >1000 | 205 | ≈1000 | 32 |
| 94 | Am | Pip-OMe | Na | 0 | 0.07 | 1.9 | 10.5 | 46 | 500 | 220 | >1000 | 35 |
| 34 | Am | Ppd(4-Me) | Na | 0 | 0.0086 | 0.14 | 4.0 | 41 | >1000 | 460 | >1000 | 16 |
| 86 | Am | Pip(4-Me)-OH | Na | 0 | 0.12 | 1.2 | 42 | 96 | >1000 | 470 | >1000 | 84 |
| 35 | Am | Pzd(4-Me) | Na | 0 | 0.036 | 1.3 | 31 | 30 | >1000 | 430 | >1000 | 85 |
| 134 | Am | THICH-3-COOH | Na | 0 | 0.018 | 0.13 | 0.67 | 42 | >1000 | >1000 | 390 | 1.5 |
| 207 | Gu | Ppd | Na | 0 | 0.40 | 4.1 | 17 | 107 | >1000 | >1000 | >1000 | >1000 |
| 190 | Ox | THICH-3-COOH | Na | 0 | 2.4 | 27 | 120 | 130 | 460 | >1000 | >1000 | >1000 |
| 203 | A | Ppd(4-Me) | Na | 0 | 8.9 | >1000 | >1000 | 210 | 270 | >1000 | >1000 | >1000 |
| 182 | AMe | Ppd(4-Me) | Na | 0 | 1.9 | 3.4 | 27 | 500 | <1000 | >1000 | 76 | >1000 |
| 171 | Am | Ppd(4-Me) | Qu | 0 | 0.34 | 3.6 | 100 | 180 | 780 | >1000 | 260 | >1000 |
| 156 | Am | Ppd(4-Me) | Na | 1 | 3.6 | 46 | 46 | 25 | 350 | 340 | >1000 | 68 |

Am = amidino, Gu = guanidino, Ox = oxamidino, A = amino, AMe = aminomethyl, Na = 2-naphthyl, Qu = 8-quinolyl Table 27 shows the toxicity values, determined in the mouse, of some representative compounds of the present invention.

TABLE 27

Approximative $LD_{50}$ in the mouse

| Compound | R¹ | R² | $LD_{50}$ p.o. mg/kg BW | $LD_{50}$ i.v. mg/kg BW |
|---|---|---|---|---|
| NAPAP | | | >800 | 54 |
| TAPAM | | | >1000 | 103 |
| 123 | Am | Pro-OH | >3000 | 188 |
| 124 | Am | Pro-OMe | >3000 | 80 |
| 83 | Am | Pip-OH | >3000 | 272 |
| 85 | Am | iNip-OH | >3000 | 43 |
| 134 | Am | THICH-3-COOH | >3000 | 29 |
| 190 | Ox | THICH-3-COOH | >3000 | >150 |
| 208 | Gu | Pip-OH | >1000 | >50 |
| 186 | AMe | iNip-OH | >3000 | 100 |

Compared with earlier tested derivatives of benzamidine-containing amino acids ($LD_{50}$ 10–50 mg/kg after i.v. application), the toxicity is considerably lower for a series of compounds of the present invention, i.e. $LD_{50}$ values of more than 50 mg/kg are found after i.v. injection. This is particularly obvious when comparing NAPAP with those compounds which also show improved pharmacokinetic properties (123, 83, 186 and 190).

Tables 28–30 show the results of studies on the pharmacokinetics of representative compounds in the present invention and, for comparison, the values with NAPAP. The compounds to be tested were administered to rats intravenously (Table 28), subcutaneously (Table 29) and orally (Table 30), respectively. After administration, blood samples were taken from experimental animals at time intervals of 2 to maximally 360 minutes and the blood level of the compounds in the samples was determined by means of HPLC.

TABLE 28

Concentration (ng/ml) of selected compounds in the plasma of rats after intravenous administration of 1 mg/kg

| Time (min) | NAPAP | 123 | 83 | 85 | 134 | 190 | 186 |
|---|---|---|---|---|---|---|---|
| 2 | 4028 | 2330 | 1903 | 2348 | 4441 | 3262 | 1840 |
| 5 | 2111 | 1180 | 928 | 1238 | 1680 | 1606 | 1256 |
| 10 | 1307 | 660 | 496 | 526 | 775 | 806 | 653 |
| 15 | 933 | 440 | 243 | 334 | 621 | 496 | 426 |
| 30 | 413 | 260 | 150 | 240 | 79 | 477 | 225 |
| 45 | 106 | 185 | 115 | 176 | 78 | 134 | 205 |
| 60 | 78 | 160 | 85 | 99 | 10 | 0 | 193 |
| 90 | — | 68 | 45 | 52 | 0 | — | 53 |
| 120 | 0 | 32 | 0 | 28 | — | — | 228 |
| 180 | — | 22 | 0 | — | — | — | — |
| 240 | — | 0 | 0 | 14 | — | — | — |

TABLE 29

Concentration (ng/ml) of selected compounds in the plasma of rats after subcutaneous administration of 5 mg/kg

| Time (min) | NAPAP | 123 | 83 | 85 | 134 | 190 | 186 |
|---|---|---|---|---|---|---|---|
| 15 | 294 | 792 | 402 | 1330 | 0 | 340 | 251 |
| 30 | 375 | 1340 | 620 | 1027 | 35 | 330 | 368 |
| 45 | 324 | 1381 | 626 | 860 | 72 | 374 | 444 |
| 60 | 361 | — | 568 | 834 | 79 | 492 | 558 |
| 90 | 330 | 1781 | 467 | 913 | 92 | 354 | 629 |
| 120 | 327 | 1603 | 415 | 977 | 145 | 270 | 534 |
| 180 | 230 | 1135 | 314 | 815 | 285 | 165 | 533 |
| 240 | 173 | 927 | 297 | 676 | 268 | 152 | 669 |
| 300 | — | — | — | 550 | 248 | 138 | 455 |
| 360 | — | — | — | — | — | 126 | 340 |

TABLE 30

Concentration (ng/ml) of selected compounds in the plasma of rats after oral administration of 100 mg/kg

| Time (min) | NAPAP | 123 | 83 | 85 | 134 | 190 | 186 |
|---|---|---|---|---|---|---|---|
| 15 | 0 | 230 | 133 | 870 | 188 | 481 | 996 |

TABLE 30-continued

Concentration (ng/ml) of selected compounds in the plasma of rats after oral administration of 100 mg/kg

| Time (min) | Compound | | | | | | |
|---|---|---|---|---|---|---|---|
| | NAPAP | 123 | 83 | 85 | 134 | 190 | 186 |
| 30 | 0 | 170 | 79 | 541 | 260 | 1113 | 800 |
| 45 | 0 | — | — | 345 | 297 | 796 | 769 |
| 60 | 0 | 100 | 50 | 120 | 260 | 574 | 1246 |
| 90 | 0 | 133 | 37 | — | — | — | 877 |
| 120 | 0 | — | 38 | 103 | 234 | 542 | 619 |
| 180 | 0 | 96 | 25 | 104 | 236 | 217 | 357 |
| 240 | — | 67 | 23 | 0 | 210 | 113 | 328 |
| 300 | — | — | — | — | 157 | 50 | 370 |
| 360 | — | — | — | — | 86 | — | 326 |

Figure 2:
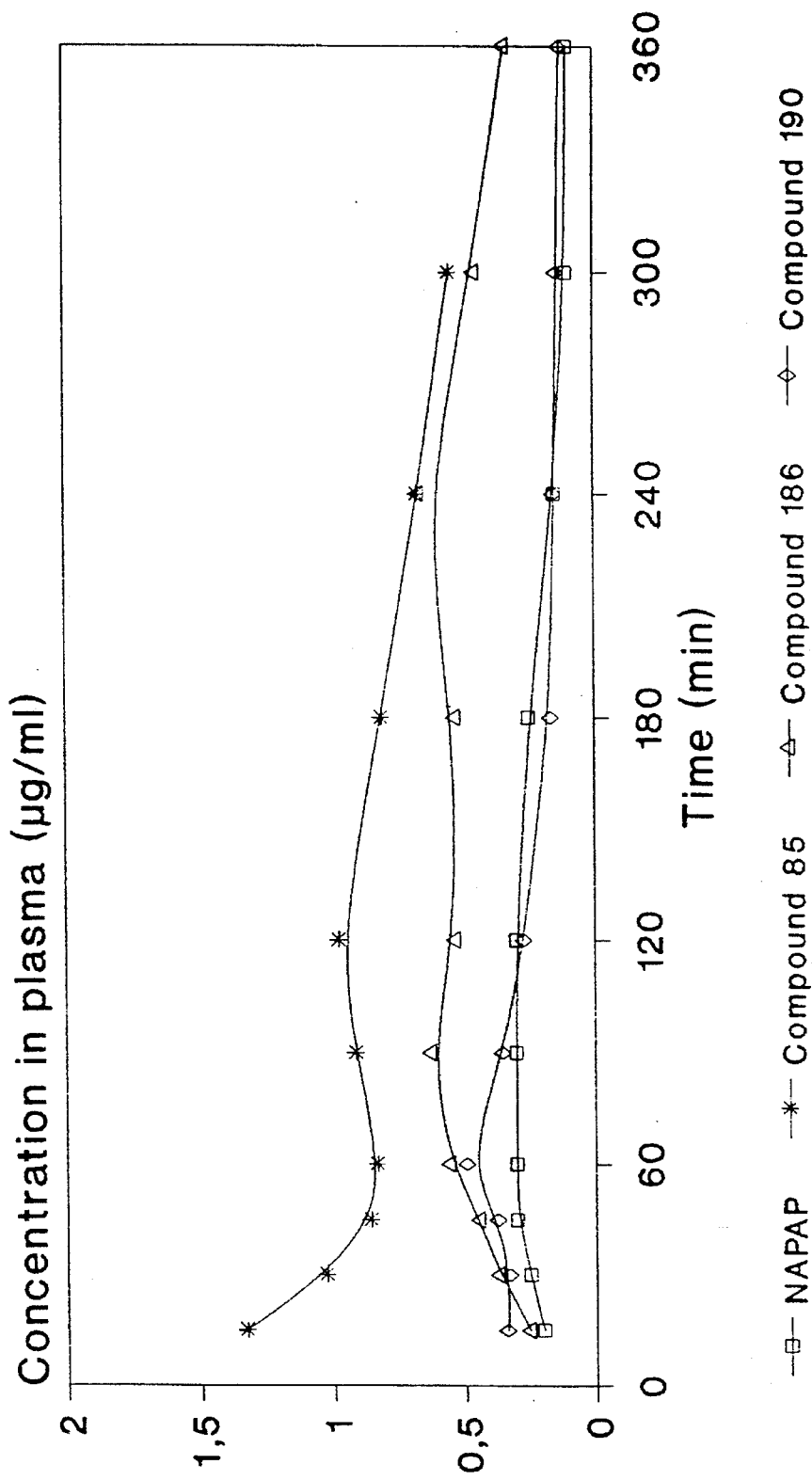

In comparison with NAPAP, the derivatives investigated show improved pharmacokinetic behaviour. Although the compounds are eliminated at comparable speed after intravenous injection (FIG. 1), relatively high, constant blood levels of the compounds are found after subcutaneous administration (FIG. 2). After oral administration, NAPAP cannot be detected in plasma, while some of the representative compounds tested in the present invention may reach comparatively high concentrations (FIG. 3).

In vitro, some of the representative compounds in the present invention have anticoagulant activity. In all cases, the thrombin time (TT) was the most prolonged value. This corresponds to the selectivity of these inhibitors which, among the clotting factors, inhibit thrombin most effectively. Prolongation of the activated partial thromboplastin time (aPTT), which is also influenced, besides thrombin time, by the enzymes which participate in the early phase of coagulation, is obtained by higher inhibitor concentrations. This also applies to the influence of the prothrombin time (PT) which represents the extrinsic coagulation pathway (illustrated for compound 34 in FIG. 4).

The anticoagulant effect of the compounds can also be demonstrated in vivo. After i.v., s.c. and p.o. administration of the compounds to be tested, the anticoagulant effect was determined in plasma of experimental animals (illustrated for compound 123 in FIG. 5). Like the concentration progression determined by means of HPLC in plasma, the antithrombin effect can be detected in the clotting test.

In practice, the phenylalanine derivatives synthesized according to one of the procedures in the present invention and used as such or as salts with a physiologically compatible mineral or organic acid are converted in appropriate forms of application by applying adequate pharmaceutical auxiliaries. Corresponding to the pharmacokinetic behaviour, there are in particular transdermal therapy systems such as plasters, but also tablets, dragées, capsules, suppositories, solutions, etc.

The dosage depends on the antithrombin activity, the toxicity, the attainable blood level, the bioavailability and the mode of application of the used compound of the present invention, as well as in general on the blood values, the weight and the general state of the patient, such that the proper dosage has to be determined by the physician. In principle, the dosage corresponds to that of known thrombin-inhibiting compounds and is comprised between about 0.2 mg/kg and about 20 mg/kg body weight; however, higher doses may also be administered. In an adult patient, the daily doses of a compound of the present invention therefore range from approximately 50 mg to approximately 1600 mg or more.

By means of compound 186, the conversion into 5 pharmaceutical forms of administration should be representatively shown.

EXAMPLE 1

Tablets with 50 mg of compound 186 as the active substance
Composition:
1 tablet contains 50 mg of active substance, 40 mg of lactose, 30 mg of cornflour and 1 mg of magnesium stearate.
Manufacturing process
The active substance mixed with lactose and cornflour is regularly soaked with a 20% ethanolic solution of polyvinylpyrrolidone, pressed through a 1.5 mm-meshed sieve and dried at 40° C. The granulate obtained in such a way is mixed with magnesium stearate and formed into tablets.

EXAMPLE 2

Dragées with 25 mg of compound 186 as the active substance
Composition:
1 dragée contains 25 mg of active substance, 20 mg of lactose and 15 mg of cornflour.
Manufacturing process
The active substance mixed with lactose and cornflour is granulated as described in example 1 and formed into oval tablet nuclei which are then coated with sugar. For this purpose, a sugar mixture consisting of 48 g of granulated sugar, 18 g of gum arabic, 48 g of wheat flour and 4 g of magnesium stearate as well as a mixture of equal parts of mucilago gum arabic and water, as a thickening agent, were used.

EXAMPLE 3

Capsules with 50 mg of compound 186 as the active substance
Composition:
1 capsule contains 50 mg of active substance and 100 mg of lactose.
Manufacturing process
The finely powdered active substance is proportionally ground with lactose and the mixture is filled in the indicated dosage into starch capsules which represent one-sidedly closed cylinders made of 2 parts that fit together.

EXAMPLE 4

Suppositories with 50 mg of compound 186 as the active substance
Composition:
1 suppository contains 50 mg of active substance and 0.95 g of cetyl phthalate as the basic substance.
Manufacturing process
500 mg of very finely powdered active substance are ground with twice as much liquefied basic substance. The preparation is mixed portionwise with the remaining liquefied basic substance and worked until a regular quality is obtained. Nearly at the limit of pourability, the mixture is poured in an adequate form and allowed to cool down at rest.

EXAMPLE 5

Injection and infusion solution, respectively, with 5 mg/ml of compound 186 as the active substance
Manufacturing process 0.5 g of active substance is diluted in 100 ml of water for injection, whereafter the solution is filtered and, if necessary, filled into 2 ml ampoules. The closed containers filled with this solution (infusion bottles, ampoules) are submitted to a steam sterilization at 121° to 124° C.

We claim:

1. L-,D-, and D,L-phenylalanine derivatives of formula I $$\begin{array}{c} R^1\text{—}C_6H_4\text{—}CH_2\text{—}CH(\text{NH}\text{—}(CO\text{—}CH(R^3)\text{—}NH)_n\text{—}SO_2\text{—}R^4)\text{—}CO\text{—}R^2 \end{array} \quad I$$

wherein n represents the number 0 or 1, $R^1$ represents a basic group of formula (a), (b), (c), (d), or (e)

$$\begin{array}{ccc}
\text{NH}=\underset{\underset{R^6}{|}}{\overset{\overset{R^6}{|}}{C}}\text{—N} & \text{NH}=\underset{\underset{\text{NH}\ R^6}{|}}{\overset{\overset{R^5}{|}}{C}}\text{—N} & \text{NH}_2\text{—C}=\text{N—OH} \\
(a) & (b) & (c)
\end{array}$$

$$\begin{array}{cc} -\text{CH}_2\text{—NH}_2 & \text{or} \quad -\text{NH}_2 \\ (d) & (e) \end{array}$$

$R^5$ and $R^6$ in formulae (a) and (b) represent hydrogen or an alkyl group of 1–2 carbon atoms, $R^2$ represents (g) a group of formula $$-\underset{\underset{R^7}{|}}{\text{N}}-\underset{\underset{R^8}{|}}{\text{CH}}-\text{CO}-R^9$$

wherein $R^7$ represents hydrogen or a straight or branched lower alkyl group, $R^8$ represents a straight or branched lower alkyl group, a 1- or 2-hydroxyethyl group, a methylmercaptoethyl group, an aminobutyl group, a guanidinopropyl group, a carboxy(lower)alkyl group, a carboxamido(lower)alkyl group, a phenyl(lower)alkyl group, the ring of which may be substituted with OH, halogen, lower alkyl or methoxy, a cyclohexyl or cyclohexylmethyl group, the ring of which may be substituted with OH, halogen, lower alkyl or methoxy, or an N-heteroaryl(lower)alkyl group wherein the heteroaryl moiety is imidazolyl or indolyl, and $R^9$ represents a hydroxyl, straight or branched lower alkoxy or a benzyloxy group, the group (g) having a racemic, or D or L configuration, respectively, (h) A group of formula $$-\text{N}\begin{array}{c} \diagup \text{CH}-(CH_2)_m \\ \diagdown \text{CH}_2-CH_2 \end{array}\begin{array}{c} | \\ \text{CO}-R^9 \end{array}$$

wherein m represents the number 1 or 2, $R^9$ represents a hydroxyl, straight or branched lower alkoxy or a benzyloxy group, and wherein one of the methylene groups may be substituted with a hydroxyl, carboxyl, lower alkyl or aralkyl group, wherein a further phenyl or cyclohexyl ring may be condensed on the heterocycloaliphatic ring of formula (h) in position 2,3 or 3,4, related to the heteroatom, the group (h) having a racemic, or D or L configuration, respectively, (i) a group of formula $$-\text{N}\begin{array}{c} \diagup (CH_2)_p-CH-CO-R^9 \\ \diagdown (CH_2)_r-CH_2 \end{array}$$

wherein p=r=1, p=1 and r=2 or p=2 and r=1, $R^9$ represents a hydroxyl, straight or branched lower alkoxy or a benzyloxy group, and wherein one of the methylene groups may be substituted with a hydroxyl, carboxyl, lower alkyl or aralkyl group, wherein a further phenyl or cyclohexyl ring may be condensed on the heterocycloaliphatic ring of formula (i) in position 2,3 or 3,4, related to the heteroatom, (k) a piperidyl group that is substituted with an alkyl group of 1–2 carbon atoms or hydroxyl group in one of the positions 2, 3, and 4, wherein a further phenyl or cyclohexyl ring may be condensed on the heterocycloaliphatic ring of formula (k) in position 2,3 or 3,4, related to the heteroatom, (l) a piperazyl group, which may be substituted in p position with a lower alkyl group or an alkoxycarbonyl group, (m) a group of formula $$-\underset{\underset{R^{10}}{|}}{\text{N}}-(CH_2)_{n'}-\text{CO}-R^9$$

wherein n' represents the numbers 1 to 6, $R^9$ represents a hydroxyl, straight or branched lower alkoxy or a benzyloxy group, and $R^{10}$ represents hydrogen or the methyl or cyclohexyl group, (n) a group of formula $$-\text{NH}-CH_2-\underset{}{\bigcirc_H}-\text{CO}-R^9$$

wherein $R^9$ represents a hydroxyl, straight or branched lower alkoxy or a benzyloxy group, and, when n=0, $R^2$ additionally represents (f) O-alkyl, O-cycloalkyl, or O-aralkyl, all having up to 8 carbon atoms, or OH, $R^3$ represents hydrogen, an alkyl group of 1–2 carbon atoms, or a 1- or 2-hydroxyethyl group, and $R^4$ represents phenyl, methylphenyl, α-naphthyl, β-naphthyl, 5-(dimethylamino)-naphthyl, or quinolyl, wherein lower alkyl denotes alkyl of 1–4 carbon atoms, or pharmaceutically acceptable salts thereof with mineral or organic acids.

2. Phenylalanine derivatives according to claim 1, wherein $R^2$ represents O-alkyl, O-cycloalkyl or O-aralkyl and n=0 or a heterocycloaliphatic group of formulae (h), (i), (k) and (l), $R^9$ in formulae (h) and (i) being possibly a hydroxyl, straight or branched lower alkoxy, or benzyloxy group, $R^4$ represents β-naphthyl, and n represents the number 0.

3. Method for the manufacture of antithrombotically active drugs to be adminstered orally, subcutaneously or intravenously which comprises formulating phenylalanine derivatives according to claim 1 with pharmaceutically acceptable carriers.

4. Anthrombotic drug to be administered orally, subcutaneously or intravenously, which contains an effective amount of a phenylalanine derivative according to claim 1 and a pharmaceutically acceptable carrier.

5. Antithrombotically active drug according to claim 4, in the form of tablets, dragees, capsules, pellets, suppositories, solutions or transdermal systems.

6. Method for blood coagulation or thrombin inhibition, respectively, in living organisms, characterized by the administration of an effective quantity of at least one compound according to claim 1.

7. Method for blood coagulation or thrombin inhibition, respectively, in living organisms, characterized by the administration of an effective quantity of a drug according to claim 4.

8. Method for blood coagulation or thrombin inhibition, respectively, in man, characterized by the administration of an effective quantity of at least one compound according to claim 1.

9. Method for blood coagulation or thrombin inhibition, respectively, in man, characterized by the administration of an effective quantity of a drug according to claim 4.

10. Antithrombotically active drug according to claim 4, wherein said transdermal systems are plasters.

* * * * *